(12) United States Patent
Fernandez et al.

(10) Patent No.: US 8,962,788 B2
(45) Date of Patent: Feb. 24, 2015

(54) PRODUCTION OF A POLYCARBONATE WITH LIMITED METAL RESIDUALS

(71) Applicant: Sabic Innovative Plastics IP B.V., Bergen op Zoom (NL)

(72) Inventors: Ignacio Vic Fernandez, Santo Angel (ES); Mykhaylo Lyakhovych, Murcia (ES); Sergio Ferrer Nadal, Granada (ES)

(73) Assignee: Sabic Global Technologies B.V. (NL)

( * ) Notice: Subject to any disclaimer, the term of this patent is extended or adjusted under 35 U.S.C. 154(b) by 0 days.

(21) Appl. No.: 14/207,806

(22) Filed: Mar. 13, 2014

(65) Prior Publication Data

US 2014/0275466 A1    Sep. 18, 2014

(30) Foreign Application Priority Data

Mar. 15, 2013    (EP) .................................... 13382085

(51) Int. Cl.
| | | |
|---|---|---|
| *C08G 64/00* | (2006.01) | |
| *C08G 64/30* | (2006.01) | |
| *C07C 69/96* | (2006.01) | |
| *C08G 63/02* | (2006.01) | |

(52) U.S. Cl.
CPC .............. *C08G 64/307* (2013.01); *C07C 69/96* (2013.01)
USPC ........ 528/196; 264/176.1; 264/219; 528/198; 528/271; 528/272

(58) Field of Classification Search
CPC ....... C08G 64/307; C08G 64/06; C08G 64/14
USPC ............... 264/176.1, 219; 528/196, 198, 271, 528/272, 165
See application file for complete search history.

(56) References Cited

U.S. PATENT DOCUMENTS

| | | |
|---|---|---|
| 5,498,319 A | 3/1996 | Ehlinger |
| 6,410,678 B1 | 6/2002 | Ishida et al. |
| 6,669,850 B1 * | 12/2003 | Fuller et al. .................... 210/660 |
| 7,812,189 B2 | 10/2010 | Fukuoka et al. |
| 2005/0014965 A1 | 1/2005 | Dahlmann et al. |
| 2011/0034588 A1 | 2/2011 | Boucher et al. |

FOREIGN PATENT DOCUMENTS

| | | |
|---|---|---|
| EP | 0633241 A1 | 1/1995 |
| GB | 883619 | 12/1961 |

OTHER PUBLICATIONS

International Search Report for International Application PCT/IB2014/059699; International Filing Date: Mar. 12, 2014; Date of Mailing: Jun. 10, 2014; 4 pages.
U.S. Appl. No. 14/206,692; the filed with USPTO on Mar. 12, 2014.

(Continued)

*Primary Examiner* — Terressa Boykin
(74) *Attorney, Agent, or Firm* — Cantor Colburn LLP

(57) ABSTRACT

A method for producing a polycarbonate comprising: reacting a diaryl carbonate with a dihydroxy compound to form a polycarbonate, wherein the polycarbonate comprises: less than or equal to 1000 ppb of molybdenum; less than or equal to 33 ppb of vanadium; less than or equal to 33 ppb of chromium; less than or equal to 375 ppb of niobium; less than or equal to 33 ppb of nickel; less than or equal to 10 ppb of zirconium; and less or equal to 10 ppb iron.

22 Claims, 13 Drawing Sheets

(56) References Cited

OTHER PUBLICATIONS

Written Opinion for International Search Report for International Application PCT/IB2014/059699; International Filing Date: Mar. 12, 2014; Date of Mailing: Jun. 10, 2014; 5 pages.

European Search Report for European Application No. 13382085.2; European Filing Date Sep. 10, 2013; Date of Mailing Oct. 1, 2013; 4 pages.

* cited by examiner

PRODUCTION OF A POLYCARBONATE WITH LIMITED METAL RESIDUALS

CROSS-REFERENCE TO RELATED APPLICATION

This application claims the benefit of European Patent Application Serial No. 13382085.2 filed Mar. 15, 2013. The related application is incorporated herein by reference.

BACKGROUND

The preparation of polycarbonate can be achieved through the melt reaction of an aromatic dihydroxy compound and a diaryl carbonate. There are several methods by which diaryl carbonate can be produced including decarbonylating a diaryl oxalate in the presence of a catalyst while removing a carbon monoxide by product; reacting an aromatic hydroxy compound with phosgene in the gas phase in the presence of a heterogeneous catalyst, for example, the direct phosgenation of phenol; reacting an aromatic hydroxy compound, carbon monoxide, and oxygen in the presence of a redox catalyst and an organic salt; or reacting an aromatic hydroxy compound with a dialkyl carbonate. A specific example of a non-phosgene route to synthesize the diaryl carbonate of diphenyl carbonate (DPC) can be achieved with the use of respective catalysts through the transesterification of dimethyl carbonate (DMC) and phenol to produce phenyl methyl carbonate (PMC) as shown in Reaction (1),

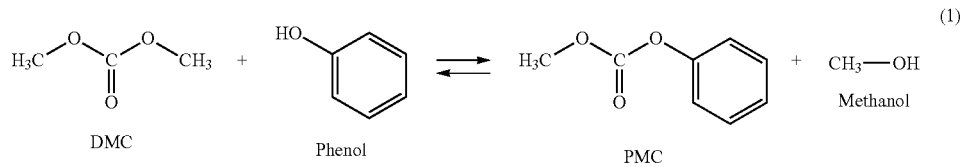

followed by the subsequent disproportionation of PMC to produce diphenyl carbonate (DPC) as shown in Reaction (2),

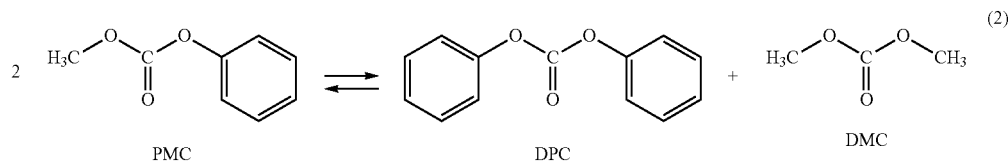

with an additional formation of small amounts of an alkyl aryl ether (anisole) as the main reaction byproduct.

The formation of diaryl carbonates in any of the aforementioned reaction schemes or in any other reaction scheme can generally be facilitated through the use of a catalyst. Unfortunately, any residual metal from said catalyst can result in discoloration of a resultant polycarbonate resulting in, for example, a reduction in the color stability of the polycarbonate. Furthermore, the metal from the catalyst used in the formation of the diaryl carbonate can cause corrosion of the reaction vessel that can result in a further source of metal corrosion, in addition to any degradation of the reaction vessel that can occur independently of the metal catalyst.

A purified diaryl carbonate reactant is therefore desirable in the production of polycarbonate for use in high transparency applications.

BRIEF SUMMARY

Disclosed herein are purified diaryl carbonates, methods of making polycarbonate, and the polycarbonate made therefrom.

In an embodiment, a purified diaryl carbonate comprises less than or equal to 500 ppb of molybdenum based on the total weight of the diaryl carbonate and the metal contaminant; less than or equal to 33 ppb of vanadium based on the total weight of the diaryl carbonate and the metal contaminant; less than or equal to 33 ppb of chromium based on the total weight of the diaryl carbonate and the metal contaminant; less than or equal to 75 ppb of titanium based on the total weight of the diaryl carbonate and the metal contaminant; less than or equal to 375 ppb of niobium based on the total weight of the diaryl carbonate and the metal contaminant; less than or equal to 33 ppb of nickel based on the total weight of the diaryl carbonate and the metal contaminant; less than or equal to 750 ppb of zirconium; and less or equal to 10 ppb iron based on the total weight of the diaryl carbonate and the metal contaminant.

In an embodiment, a method for producing a polycarbonate comprises reacting a diaryl carbonate with a dihydroxy compound to form a polycarbonate, wherein the polycarbonate comprises: less than or equal to 500 ppb of molybdenum based on the total weight of the diaryl carbonate and the metal contaminant; less than or equal to 33 ppb of vanadium based on the total weight of the diaryl carbonate and the metal contaminant; less than or equal to 33 ppb of chromium based on the total weight of the diaryl carbonate and the metal contaminant; less than or equal to 75 ppb of titanium based on the total weight of the diaryl carbonate and the metal contaminant; less than or equal to 375 ppb of niobium based on the total weight of the diaryl carbonate and the metal contaminant; less than or equal to 33 ppb of nickel based on the total weight of the diaryl carbonate and the metal contaminant; less than or equal to 750 ppb of zirconium based on the total weight of the diaryl carbonate and the metal contaminant; and less or equal to 10 ppb iron based on the total weight of the diaryl carbonate and the metal contaminant.

In an embodiment, a method for producing a polycarbonate comprises selecting a diaryl carbonate based on a maximum contaminant content and reacting the diaryl carbonate with a dihydroxy compound to form a melt polycarbonate comprising less than or equal to 500 ppb of molybdenum based on the total weight of the diaryl carbonate and the metal contaminant; less than or equal to 33 ppb of vanadium based on the total weight of the diaryl carbonate and the metal contaminant; less than or equal to 33 ppb of chromium based on the total weight of the diaryl carbonate and the metal contaminant; less than or equal to 75 ppb of titanium based on the total weight of the diaryl carbonate and the metal contaminant; less than or equal to 375 ppb of niobium based on the total weight of the diaryl carbonate and the metal contaminant; less than or equal to 33 ppb of nickel based on the total weight of the diaryl carbonate and the metal contaminant; less than or equal to 750 ppb of zirconium based on the total weight of the diaryl carbonate and the metal contaminant; and less or equal to 10 ppb iron based on the total weight of the diaryl carbonate and the metal contaminant. The reacting occurs in at least one reactor, and wherein the reactor comprises a reactor contaminant.

In still another embodiment, a purified diaryl carbonate can comprise: less than or equal to 25 ppb of vanadium based on the total weight of the diaryl carbonate and the metal contaminant; less than or equal to 33 ppb of nickel based on the total weight of the diaryl carbonate and the metal contaminant; less than or equal to 750 ppb of zirconium; and less or equal to 10 ppb iron based on the total weight of the diaryl carbonate and the metal contaminant.

These and other features and characteristics are more particularly described below in view of the figures and detailed description.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Figure 1:
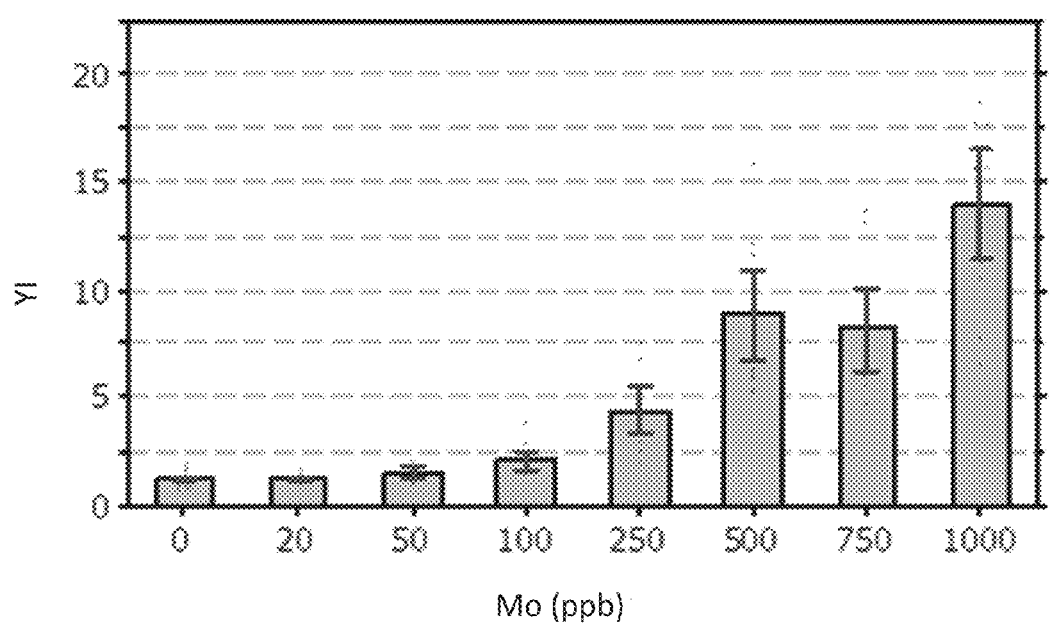
FIG. 1 is a graphical illustration of the effect of molybdenum levels on yellowness index.

Synthetic routes to produce diaryl carbonate can result in metal contaminated diaryl carbonate compositions and/or contaminated aryl alkyl carbonate compositions. The metal contaminant can arise from one or both of the use of a catalyst to facilitate the formation of the diaryl carbonate and the corrosion of metal machinery (e.g., that can arise due to the presence of said catalyst). The metal contaminants can be in organometallic or inorganic forms. It was surprisingly found that metal contaminant levels in polycarbonate of less than or equal to 500 parts per billion by weight (ppb), specifically, less than or equal to 200 ppb of molybdenum, more less than or equal to 33 ppb of molybdenum, and even more specifically, less than or equal to 20 ppb of molybdenum; less than or equal to 33 ppb, specifically, less than or equal to 20 ppb vanadium; less than or equal to 33 ppb, specifically, less than or equal to 20 ppb chromium; less than or equal to 75 ppb, specifically, less than or equal to 50 ppb titanium; less than or equal to 375 ppb, specifically, less than or equal to 250 ppb of niobium; less than or equal to 33 ppb, specifically, less than or equal to 20 ppb of nickel; less than or equal to 750 ppb, specifically, less than or equal to 200 ppb, more specifically, less than or equal to 10 ppb, specifically, less than or equal to 5 ppb zirconium; less than or equal to 10 ppb, specifically, less than or equal to 5 ppb of iron had little to no effect on the resultant yellowness index of the polycarbonate. Unless stated otherwise, the weights of the respective metal contaminant are based on the total weight of the diaryl carbonate and the total weight of the metal contaminant. It was surprisingly found that molybdenum amounts of greater than 500 ppb, for example, 1000 ppb resulted in increased yellowness index as compared to a polycarbonate that is free of molybdenum. It was also surprisingly found that amounts of greater than 33 ppb vanadium in the polycarbonate resulted in increased yellowness index as compared to a polycarbonate that is free of vanadium. In other words, it was found that if the level of metal contaminants is at or below these levels, the metal contaminants will not contribute to the yellowness index (YI) of the polycarbonate, thereby producing an improved polycarbonate, wherein the yellowness index is determined in accordance with ASTM D1925.

Assuming that the metal contaminant arises solely from the diaryl carbonate, the diaryl carbonate used in the polymerization of the polycarbonate can comprise less than or equal to 500 ppb, specifically, less than or equal to 33 ppb of molybdenum, more specifically, less than or equal to 23 ppb of molybdenum; less than or equal to 38 ppb, specifically, less than or equal to 23 ppb vanadium; less than or equal to 38 ppb, specifically, less than or equal to 23 ppb chromium; less than or equal to 85 ppb, specifically, less than or equal to 57 ppb titanium; less than or equal to 425 ppb, specifically, less than or equal to 284 ppb of niobium; less than or equal to 38 ppb, specifically, less than or equal to 23 ppb of nickel; less than or equal to 750 ppb, specifically, less than or equal to 500 ppb, and even less than or equal to 200 ppb zirconium, for example, less than or equal to 12 ppb, specifically, less than or equal to 6 ppb zirconium; and less than or equal to 12 ppb, specifically, less than or equal to 6 ppb of iron.

The diaryl carbonate that can be purified can have the formula (I)

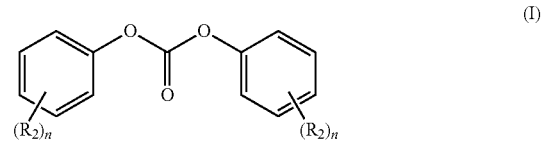

wherein n is an integer 1 to 3 and each $R_2$ is independently linear or branched, optionally substituted $C_{1-34}$ alkyl, specifically, $C_{1-6}$ alkyl, more specifically, $C_{1-4}$ alkyl; $C_{1-34}$ alkoxy, specifically, $C_{1-6}$ alkoxy, more specifically, $C_{1-4}$ alkoxy; $C_{5-34}$ cycloalkyl; $C_{7-34}$ alkylaryl; $C_{6-34}$ aryl; or a halogen radical, specifically, a chlorine radical. $R_2$ can also represent —COO—R', wherein R' can be H; optionally branched $C_{1-34}$ alkyl, specifically, $C_{1-6}$ alkyl, more specifically, $C_{1-4}$ alkyl; $C_{1-34}$ alkoxy, specifically, $C_{1-16}$ alkoxy, specifically, $C_{1-4}$ alkoxy; $C_{5-34}$ cycloalkyl; $C_{7-34}$ alkylaryl; or $C_{6-34}$ aryl.

The diaryl carbonate of the general formula (I) can comprise diphenyl carbonate, methylphenyl-phenyl carbonates and di-(methylphenyl) carbonates (wherein the methyl group can be in any desired position on the phenyl rings, for example, 2,4-, 2,6-, 3,5- or 3,4-dimethylphenyl), dimethylphenyl-phenyl carbonates and di-(dimethylphenyl) carbonates (wherein the chloro atoms can be in any desired position on the phenyl rings, for example, 2-, 3-, or 4-chlorophenyl), chlorophenyl-phenyl carbonates and di-(chlorophenyl) carbonates (wherein the methyl group can be in any desired position on the phenyl rings), 4-ethylphenyl-phenyl carbonate, di-(4-ethylphenyl) carbonate, 4-n-propylphenyl-phenyl carbonate, di-(4-n-propylphenyl) carbonate, 4-isopropylphenyl-phenyl carbonate, di-(4-isopropylphenyl) carbonate, 4-n-butylphenyl-phenyl carbonate, di-(4-n-butylphenyl) carbonate, 4-isobutylphenyl-phenyl carbonate, di-(4-isobutylphenyl) carbonate, 4-tert-butylphenyl-phenyl carbonate, di-(4-tert-butylphenyl) carbonate, 4-n-pentylphenyl-phenyl carbonate, di-(4-npentylphenyl) carbonate, 4-n-hexylphenyl-phenyl carbonate, di-(4-n-hexylphenyl) carbonate, 4-isooctylphenyl-phenyl carbonate, di-(4-isooctylphenyl) carbonate, 4-n-nonylphenyl-phenyl carbonate, di-(4-n-nonyl-phenyl) carbonate, 4-cyclohexylphenyl-phenyl carbonate, di-(4-cyclohexylphenyl) carbonate, 4-(1-methyl-1-phenylethyl)-phenyl-phenyl carbonate, di-[4-(1-methyl-1-phenylethyl)-phenyl]carbonate, biphenyl-4-yl-phenyl carbonate, di-(biphenyl-4-yl) carbonate, (1-naphthyl)-phenyl carbonate, (2-naphthyl)-phenyl carbonate, di-(1-naphthyl) carbonate, di-(2-naphthyl) carbonate, 4-(1-naphthyl)-phenyl-phenyl carbonate, 4-(2-naphthyl)-phenyl-phenyl carbonate, di-[4-(1-naphthyl)-phenyl]carbonate, di-[4-(2-naphthyl)phenyl]carbonate, 4-phenoxyphenyl-phenyl carbonate, di-(4-phenoxyphenyl) carbonate, 3-pentadecylphenyl-phenyl carbonate, di-(3-pentadecylphenyl) carbonate, 4-tritylphenyl-phenyl carbonate, di-(4-tritylphenyl) carbonate, methyl salicylate-phenyl carbonate, di-(methyl salicylate) carbonate, ethyl salicylate-phenyl carbonate, di-(ethyl salicylate) carbonate, n-propyl salicylate-phenyl carbonate, di-(n-propyl salicylate) carbonate, isopropyl salicylate-phenyl carbonate, di-(isopropyl salicylate) carbonate, n-butyl salicylate-phenyl carbonate, di-(n-butyl salicylate) carbonate, isobutyl salicylate-phenyl carbonate, di-(isobutyl salicylate) carbonate, tert-butyl salicylate-phenyl carbonate, di-(tert-butyl salicylate) carbonate, di-(phenyl salicylate)-carbonate, di-(benzyl salicylate) carbonate, and combinations comprising one or more of the foregoing. The diaryl carbonate can comprise diphenyl carbonate.

There are several methods by which diaryl carbonate can be produced. One method for producing diaryl carbonate includes decarbonylating a diaryl oxalate (such as diphenyl oxalate) in the presence of a decarbonylation catalyst while removing a carbon monoxide by product. The decarbonylation reaction can occur in the liquid phase. The diaryl oxalate can comprise a diaryl oxalate of the formula: ArO(C=O)—(C=O)OAr, where each Ar independently can be an aromatic hydrocarbon group having 6 to 14 carbon atoms, for example, Ar can be a phenyl group, which can be substituted with at least one selected from alkyl groups having 1 to 6 carbon atoms (such as methyl, ethyl, propyl, butyl, pentyl, and hexyl), alkoxy groups having 1 to 6 carbon atoms (such as methoxy, propoxy, butoxy, pentoxy, and hexoxy), and halogen atoms (such as fluorine, chlorine, bromine, and iodine). The diaryl oxalate can comprise diphenyl oxalate, m-cresyl oxalate, m-cresyl phenyl oxalate, p-cresyl oxalate, p-cresyl phenyl oxalate, dinaphthyl oxalate, bis(diphenyl)oxalate, bis(chlorophenyl)oxalate, or a combination comprising of one or more of the forgoing. The diaryl oxalate can contain less than or equal to 5 parts per million by weight (ppm), specifically, less than or equal to 2 ppm of a hydrolysable halogen.

The diaryl oxalate can be prepared by transesterifying a dialkyl oxalate (such as dimethyl oxalate) with a hydroxyaryl compound (such as phenol) in the presence of a transesterification catalyst, where the transesterification reaction can occur in the liquid phase. The dialkyl oxalate can comprise one or more lower dialkyl oxalates of which the alkyl group comprises 1 to 6 carbon atoms, for example, dimethyl oxalate, diethyl oxalate, dipropyl oxalate, dibutyl oxalate, dipentyl oxalate, and dihexyl oxalate.

The transesterification catalyst useful for the preparation of the diaryl oxalate from the dialkyl oxalate and the hydroxyaryl compound can comprise at least one of, for example, compounds and complexes of alkali metals, compounds and complexes of cadmium and zirconium, lead-containing compounds, iron-containing compounds, copper group metal compounds, silver-containing compounds, zinc-containing compounds, organic tin compounds, and Lewis acid compounds of aluminum, titanium, and vanadium. The decarbonylation catalyst can comprise at least one organic phosphorus compound (such as an organic phosphine compound, an organic phosphine oxide compound, an organic phosphine dihalide compound, and an organic phosphonium salt compound). The decarbonylation catalyst can contain a halogen, for example, on the phosphorus containing compound or as a separate halogen compound.

Another method for producing diaryl carbonate includes reacting an aromatic hydroxy compound and carbon monoxide in the presence of oxygen, where the reaction can be facilitated by a catalyst and an optional organic salt. For example, the reaction can be the oxidative carbonylation of phenol, where the reaction can occur in a fixed-bed reactor or in an autoclave reactor. Suitable catalysts for the oxidative carbonylation of aromatic hydroxy compounds include a palladium catalyst. The palladium catalyst can be in solvated form (such as $PdBr_2$ promoted with transition metal oxides and solvated promoters, including one or more of $N(Bu)_4Br$, $Mn(AcAc)_2$, $NaO(C_6H_5)$ and the like), suspended form with Pd supported on pulverized $TiO_2$, or extrudated form with Pd supported on rare earth metal oxide. The palladium catalyst can comprise $Pd(OAc)_2$/hydrotalcite. As used herein Bu means butyl, AcAc means acetylacetonate, and OAc means acetate. The catalyst can comprise a cocatalyst, such as a cesium compound, a manganese compound, a cobalt compound, a copper compound, hydroquinone, benzoquinone, naphthoquinone, or a combination comprising one or more of the foregoing. The organic salt can comprise, for example, "$Bu_4NBr$, "$Bu_4PBr$, PPNBr, and the like.

The aromatic hydroxy compound can comprise an aromatic hydroxy compound of the formula (III)

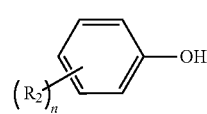

(III)

wherein n and $R_2$ are defined as above in formula (I).

The aromatic hydroxy compound can comprise phenol, o-, m- or p-cresol, dimethylphenol (wherein the methyl groups can be in any desired position on the phenol ring, for example, 2,4-, 2,6- or 3,4-dimethylphenol), o-, m- or p-chlorophenol, o-, m- or p-ethylphenol, o-, m- or p-n-propylphenol), 4-isopropylphenol, 4-n-butylphenol, 4-isobutylphenol, 4-tert-butylphenol, 4-n-pentylphenol, 4-n-hexylphenol, 4-isooctylphenol, 4-n-nonylphenol, o-, m- or p-methoxyphenol, 4-cyclohexylphenol, 4-(1-methyl-1-phenylethyl)-phenol, biphenyl-4-ol, 2-naphthol, 2-1-naphthol, 4-(1-naphthyl)phenol, 4-(2-naphthyl)phenol, 4-phenoxyphenol, 3-pentadecylphenol, 4-tritylphenol, salicylic acid methyl ester, salicylic acid ethyl ester, salicylic acid n-propyl ester, salicylic acid isopropyl ester, salicylic acid n-butyl ester, salicylic acid isobutyl ester, salicylic acid tert-butyl ester, salicylic acid phenyl ester, salicylic acid benzyl ester, or a combination comprising one or more of the foregoing.

The aromatic hydroxy compound can comprise phenol, 4-tert-butylphenol, biphenyl-4-ol, 4-(1-methyl-1-phenylethyl)-phenol, or a combination comprising one or more of the foregoing.

Other methods for producing diaryl carbonate include 1) reacting an aromatic hydroxy compound with phosgene in either the gas or liquid phase, for example, the direct phosgenation of phenol and 2) reacting an aromatic hydroxy compound with a dialkyl carbonate, where said reactions can occur in the presence of a transesterification catalyst. The aromatic hydroxy compound and either phosgene or the dialkyl carbonate can be added in a molar ratio of 1:0.1 to 1:10, specifically, 1:0.2 to 1:5, more specifically, 1:0.5 to 1:3. The indicated molar ratio does not take into account any recycled components that can be added back to the production column.

The dialkyl carbonate can comprise the dialkyl carbonate of the formula (III)

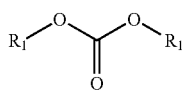

(II)

wherein each $R_1$ independently is linear or branched; optionally substituted; $C_{1-34}$ alkyl, specifically, $C_{1-6}$ alkyl, more specifically, $C_{1-4}$ alkyl. The $C_{1-4}$ alkyl can comprise methyl, ethyl, n-propyl, isopropyl, n-butyl, sec-butyl, tert-butyl, or a combination comprising of one or more of the foregoing. The $C_{1-6}$ alkyl can comprise n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, or a combination comprising of one or more of the foregoing. The $C_1$-$C_{34}$-alkyl can comprise n-heptyl, n-octyl, pinacyl, adamantyl, an isomeric menthyl, n-nonyl, n-decyl, n-dodecyl, n-tridecyl, n-tetradecyl, n-hexadecyl, or n-octadecyl, or a combination comprising of one or more of the foregoing.

The dialkyl carbonates can comprise dimethyl carbonate, diethyl carbonate, dipropyl carbonate (e.g., di(n-propyl) carbonate, and/or di(isopropyl) carbonate), dibutyl carbonate (e.g., di(n-butyl) carbonate, di(sec-butyl) carbonate, and/or di(tert-butyl) carbonate), dihexyl carbonate, or a combination comprising one or more of the foregoing.

A catalyst can be used to facilitate the reaction between the aromatic hydroxy compound and either phosgene or the dialkyl carbonate. The catalyst can be a homogeneous catalyst and/or a heterogeneous catalyst, wherein a heterogeneous catalyst comprises two or more catalysts. The catalyst can comprise hydrides, oxides, hydroxides, alcoholates, amides and other salts of alkali and alkaline earth metals, such as of lithium, sodium, potassium, rubidium, cesium, magnesium and calcium, specifically, lithium, sodium, potassium, magnesium, calcium, or a combination comprising one or more of the foregoing. Salts of the alkali and alkaline earth metals can also be salts of organic or inorganic acids, such as of acetic acid, propionic acid, butyric acid, benzoic acid, stearic acid, carbonic acid (carbonates or hydrogen carbonates), phosphoric acid, hydrocyanic acid, thiocyanic acid, boric acid, cinnamic acid, $C_{14}$-stannonic acids, antimonic acid, or a combination comprising one or more of the foregoing. Suitable compounds of the alkali and alkaline earth metals can be the oxides, hydroxides, alcoholates, acetates, propionates, benzoates, carbonates, and hydrogen carbonates. The mentioned alkali or alkaline earth metal compounds can be used in amounts of 0.001 to 2 wt %, specifically, 0.005 to 0.9 wt %, and more specifically, 0.01 to 0.5 wt %, based on the weight of the reaction mixture to be reacted.

Further catalysts which can be used can comprise a metal such as titanium, lead, tin, zirconium, molybdenum, niobium, vanadium, uranium, iron, zinc, aluminum, yttrium, lanthanum, hafnium, tungsten, neodymium, samarium, ytterbium, copper, or a combination comprising one or more of the foregoing. Such metals can be used in metal catalyst compounds such as $AlX_3$, $TiX_3$, $UX_4$, $TiX_4$, $VOX_3$, $VX_5$, $ZnX_2$, $FeX_3$, $PbX_2$ and $SnX_4$, wherein X represents halogen, acetoxy, alkoxy, aryloxy radicals, or a combination comprising one or more of the foregoing. The metal compound of $AlX_3$, $TiX_4$, $PbX_2$, and $SnX_4$ can comprise titanium tetrachloride, titanium tetramethoxide, titanium tetraphenoxide, titanium tetraethoxide, titanium tetraisopropylate, titanium tetradodecylate, tin tetraisooctylate and aluminium triisopropylate. The mentioned metal compounds can be used in an amount of 0.001 to 15 wt %, more specifically, 0.005 to 10 wt %, and even more specifically, 0.01 to 7 wt %, based on the weight of the reaction mixture.

Further catalysts which can be used can be organotin compounds of the general formula $(R^{11})_{4-x}$—$Sn(Y)_x$, wherein Y represents a radical $OCOR^{12}$, OH, or OR, wherein $R^{12}$ represents $C_{1-12}$ alkyl, $C_{6-12}$ aryl or $C_{7-13}$ alkylaryl, $R^{11}$ independently of $R^{12}$ has the meaning of $R^{12}$ and x represents an integer 1 to 3; dialkyltin compounds having from 1 to 12 carbon atoms in the alkyl radical; or bis-(trialkyltin) compounds, for example, trimethyltin acetate, triethyltin benzoate, tributyltin acetate, triphenyltin acetate, dibutyltin diacetate, dibutyltin dilaurate, dioctyltin dilaurate, dibutyltin adipinate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctylate, octyltin triisooctylate, butylstannonic acid, octylstannonic acid, or a combination comprising one or more of the foregoing. The organotin compound can be used in an amount of 0.001 to 20 wt %. The organotin compound can comprise polymeric tin compounds of the formula —[—$RR^{11}Sn$—O—]—, in which R and $R^{11}$ independently of one another have the meaning given above for $R^{12}$, for example, poly[oxy(dibutylstannylene)], poly[oxy(dioctyl stannylene)], poly[oxy(butylphenyl stannylene)], and poly [oxy(diphenylstannylene)], polymeric hydroxystannoxanes of the formula —[—RSn(OH)—O—]—, for example, poly (ethylhydroxystannoxane), poly(butylhydroxystannoxane), poly(octylhydroxysnoxane), poly(undecylhydroxystannoxane), and poly(dodecylhydroxystannoxanes), or a combination comprising one or more of the foregoing. The polymeric tin compounds can be used in an amount of 0.001 to 20 wt %, specifically, 0.005 to 5 wt %, based on dialkyl carbonate. Further tin compounds, which can be used are Sn(II) oxides of the general formula X—$R^{13}$Sn—O—$R^{13}$Sn—Y, wherein X and Y independently of one another represent OH, SCN, $OR^{14}$, $OCOR^{14}$ or halogen and $R^{13}$ represents alkyl, aryl, wherein $R^{14}$ has the meaning given above for $R^{12}$.

Further catalysts are lead compounds, optionally together with triorgano-phosphanes, a chelate compound or an alkali metal halide, for example, $Pb(OH)_2 \cdot 2PbCO_3$, $Pb(OCO—CH_3)_2$, $Pb(OCO—CH_3)_2 \cdot 2LiCl$, $Pb(OCO—CH_3)_3 \cdot 2PPh_3$ in amounts of 0.001 to 1, specifically, 0.005 to 0.25 mole per mole of dialkyl carbonate, as well as other lead(II) and lead (IV) compounds, such as PbO, $PbO_2$, red lead, lead diphenoxide, plumbites and plumbates, iron(III) acetate, also copper salts and/or metal complexes, for example, of alkali, zinc, titanium, and iron.

It is further possible to use heterogeneous catalyst systems. Such systems are, for example, mixed oxides of silicon and titanium which are obtainable by common hydrolysis of silicon and titanium halides or titanium dioxides having a high BET surface area>20 meters squared per gram ($m^2$/g).

The catalyst, when homogeneous, can be introduced to the reaction mixture in dissolved or suspended form together with the stream containing the aromatic hydroxy compound. Alternatively, the catalyst can be introduced, for example, in the reaction alcohol or a suitable inert solvent. A heterogeneous catalyst can be used in a packed bed, a column, or in special catalytic distillation arrangements, as well as in other arrangements.

As mentioned above, metal from the catalyst used in the production of the diaryl carbonate can cause corrosion of any metal machinery the process mixture comes in contact with, such as one or more of the reaction vessels, distillation columns, heat exchangers, pumps, compressors, storage tanks, instrumentation, transport pipes, and mixing blades. The metal machinery can comprise a metal, where the metal can comprise steel. The corrosion of the process vessel can result in the release of a metal, such as iron, chromium, nickel, molybdenum, copper, titanium, zinc, aluminum, vanadium, niobium, zirconium, manganese, or a combination comprising one or more of the foregoing.

The diaryl carbonate can be purified using one or more separation columns, in which the mixture comprising the diaryl carbonate and the metal contaminant is introduced to a high boiling point material separating column where a purified diaryl carbonate is produced as a top component and diaryl carbonate containing the metal contaminant exits as a bottom component. Alternatively, or in addition, the diaryl carbonate can be purified by methods such as melt crystallization, adduct crystallization, liquid-liquid extraction, solid-liquid extraction, and combinations comprising at least one of the foregoing.

The purification method can result in a purified diaryl carbonate that comprises less than or equal to 38 parts per billion by weight (ppb), specifically, less than or equal to 23 ppb of molybdenum; less than or equal to 38 ppb, specifically, less than or equal to 23 ppb vanadium; less than or equal to 38 ppb, specifically, less than or equal to 23 ppb chromium; less than or equal to 85 ppb, specifically, less than or equal to 57 ppb titanium; less than or equal to 425 ppb, specifically, less than or equal to 284 ppb of niobium; less than or equal to 38 ppb, specifically, less than or equal to 23 ppb of nickel; less than or equal to 750 ppb, specifically, less than or equal to 200 ppb, more specifically less than or equal to 12 ppb, or less than or equal to 6 ppb zirconium; and less than or equal to 12 ppb, specifically, less than or equal to 6 ppb of iron. The diaryl carbonate can comprise less than or equal to 38 ppb, specifically, less than or equal to 23 ppb, more specifically, less than 20 ppb vanadium. The diaryl carbonate can comprise less than or equal to 500 ppb, specifically, less than or equal to 38 ppb, more specifically, less than 23 ppb molybdenum. The diaryl carbonate can be used to produce polycarbonate with a metal levels of less than or equal to 33 parts per billion by weight (ppb), specifically, less than or equal to 20 ppb of molybdenum; less than or equal to 33 ppb, specifically, less than or equal to 20 ppb vanadium; less than or equal to 33 ppb, specifically, less than or equal to 20 ppb chromium; less than or equal to 75 ppb, specifically, less than or equal to 50 ppb titanium; less than or equal to 375 ppb, specifically, less than or equal to 250 ppb of niobium; less than or equal to 33 ppb, specifically, less than or equal to 20 ppb of nickel; less than or equal to 750 ppb, specifically, specifically, less than or equal to 500 ppb, more specifically, less than or equal to 200 ppb zirconium, for example, less than or equal to 10 ppb, specifically, less than or equal to 5 ppb zirconium; and less than or equal to 10 ppb, specifically, less than or equal to 5 ppb of iron. For example, where greater than or equal to 95 wt %, specifically, 99.9 wt %, even more specifically, 100 wt % the metal contaminant based on the total weight of the metal contaminant originates from the diaryl carbonate. The polycarbonate can comprise less than or equal to 38 ppb, specifically, less than or equal to 23 ppb, more specifically, less than 20 ppb vanadium based on the total weight of the diaryl carbonate and the metal contaminant. The polycarbonate can comprise less than or equal to 500 ppb, specifically, less than or equal to 38 ppb, more specifically, less than 23 ppb molybdenum based on the total weight of the diaryl carbonate and the metal contaminant.

The purified diaryl carbonate can be used as a reactant along with a dihydroxy compound in the polymerization of a polycarbonate.

A "polycarbonate" means compositions having repeating structural carbonate units of formula (1)

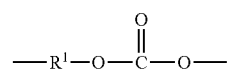

(1)

in which the $R^1$ groups contain aliphatic, alicyclic, and/or aromatic moieties (e.g., greater than or equal to 30 percent, specifically, greater than or equal to 60 percent, of the total number of $R^1$ groups can contain aromatic moieties and the balance thereof are aliphatic, alicyclic, or aromatic). Optionally, each $R^1$ can be a $C_{6-30}$ aromatic group, that is, can contain at least one aromatic moiety. $R^1$ can be derived from a dihydroxy compound of the formula HO—$R^1$—OH, in particular of formula (2)

$$HO-A^1-Y^1-A^2-OH \qquad (2)$$

wherein each of $A^1$ and $A^2$ is a monocyclic divalent aromatic group and $Y^1$ is a single bond or a bridging group having one or more atoms that separate $A^1$ from $A^2$. One atom can separate $A^1$ from $A^2$. Specifically, each $R^1$ can be derived from a dihydroxy aromatic compound of formula (3)

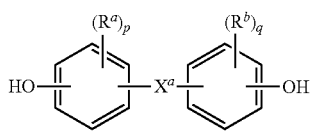

(3)

wherein $R^a$ and $R^b$ are each independently a halogen, $C_{1-12}$ alkoxy, or $C_{1-12}$ alkyl; and p and q are each independently integers of 0 to 4. It will be understood that $R^a$ is hydrogen when p is 0, and likewise $R^b$ is hydrogen when q is 0. Also in formula (3), $X^a$ is a bridging group connecting the two hydroxy-substituted aromatic groups, where the bridging group and the hydroxy substituent of each $C_6$ arylene group are disposed ortho, meta, or para (specifically, para) to each other on the $C_6$ arylene group. The bridging group $X^a$ can be single bond, —O—, —S—, —S(O)—, —S(O)$_2$—, —C(O)—, or a $C_{1-18}$ organic group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. p and q can each be 1, and $R^a$ and $R^b$ are each a $C_{1-3}$ alkyl group, specifically, methyl, disposed meta to the hydroxy group on each arylene group.

$X^a$ can be a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene.

$X^a$ can be a $C_{1-18}$ alkylene group, a $C_{3-18}$ cycloalkylene group, a fused $C_{6-18}$ cycloalkylene group, or a group of the formula —$B^1$-G-$B^2$— wherein $B^1$ and $B^2$ are the same or different $C_{1-6}$ alkylene group and G is a $C_{3-12}$ cycloalkylidene group or a $C_{6-16}$ arylene group. For example, $X^a$ can be a substituted $C_{3-18}$ cycloalkylidene of formula (4)

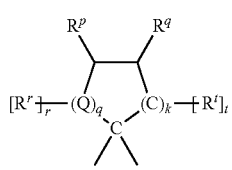

(4)

wherein $R^r$, $R^p$, $R^q$, and $R^t$ are each independently hydrogen, halogen, oxygen, or $C_{1-12}$ hydrocarbon groups; Q is a direct bond, a carbon, or a divalent oxygen, sulfur, or —N(Z)— where Z is hydrogen, halogen, hydroxy, $C_{1-12}$ alkyl, $C_{1-12}$ alkoxy, or $C_{1-12}$ acyl; r is 0 to 2, t is 1 or 2, q is 0 or 1, and k is 0 to 3, with the proviso that at least two of $R^r$, $R^p$, $R^q$, and $R^t$ taken together are a fused cycloaliphatic, aromatic, or heteroaromatic ring. It will be understood that where the fused ring is aromatic, the ring as shown in formula (4) will have an unsaturated carbon-carbon linkage where the ring is fused. When k is one and i is 0, the ring as shown in formula (4) contains 4 carbon atoms, when k is 2, the ring as shown in formula (4) contains 5 carbon atoms, and when k is 3, the ring contains 6 carbon atoms. Two adjacent groups (e.g., $R^q$ and $R^t$ taken together) can form an aromatic group or $R^q$ and $R^t$ taken together can form one aromatic group and $R^r$ and $R^p$ taken together form a second aromatic group. When $R^q$ and $R^t$ taken together form an aromatic group, $R^p$ can be a double-bonded oxygen atom, i.e., a ketone.

Bisphenols (4) can be used in the manufacture of polycarbonates containing phthalimidine carbonate units of formula (4a)

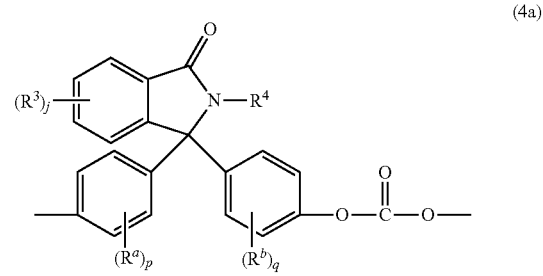

(4a)

wherein $R^a$, $R^b$, p, and q are as in formula (4), $R^3$ is each independently a $C_{1-6}$ alkyl group, j is 0 to 4, and $R_4$ is a $C_{1-6}$ alkyl, phenyl, or phenyl substituted with up to five $C_{1-6}$ alkyl groups. The phthalimidine carbonate units can be of formula (4b)

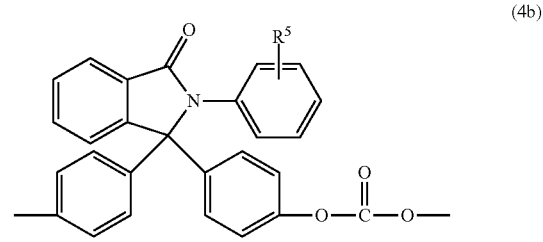

(4b)

wherein $R^5$ is hydrogen or a $C_{1-6}$ alkyl. $R^5$ can be hydrogen. Carbonate units (4a) wherein $R^5$ is hydrogen can be derived from 2-phenyl-3,3'-bis(4-hydroxy phenyl)phthalimidine (also known as N-phenyl phenolphthalein bisphenol, or "PPPBP") (also known as 3,3-bis(4-hydroxyphenyl)-2-phenylisoindolin-1-one).

Other bisphenol carbonate repeating units of this type are the isatin carbonate units of formula (4c) and (4d)

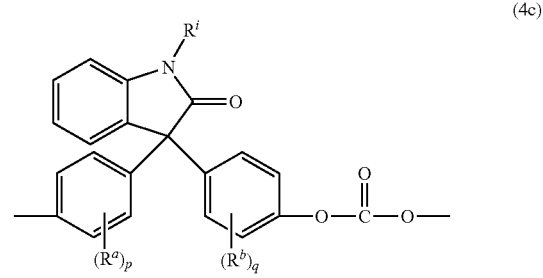

(4c)

-continued (4d)

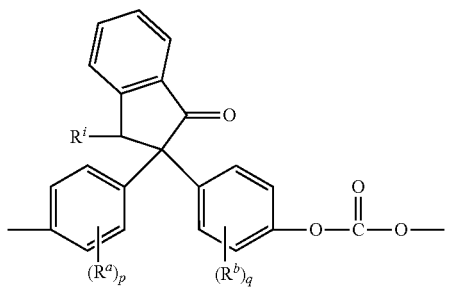

wherein $R^a$ and $R^b$ are each independently $C_{1-12}$ alkyl, p and q are each independently 0 to 4, and $R^i$ is $C_{1-12}$ alkyl, phenyl, optionally substituted with 1 5 to $C_{1-10}$ alkyl, or benzyl optionally substituted with 1 to 5 $C_{1-10}$ alkyl. $R^a$ and $R^b$ can each be methyl, p and q can each independently be 0 or 1, and $R^i$ can be $C_{1-4}$ alkyl or phenyl.

Examples of bisphenol carbonate units derived from bisphenols (4) wherein $X^b$ is a substituted or unsubstituted $C_{3-18}$ cycloalkylidene include the cyclohexylidene-bridged, alkyl-substituted bisphenol of formula (4e)

(4e)

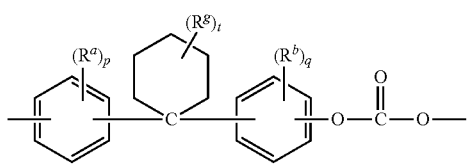

wherein $R^a$ and $R^b$ are each independently $C_{1-12}$ alkyl, $R^g$ is $C_{1-12}$ alkyl, p and q are each independently 0 to 4, and t is 0 to 10. At least one of each of $R^a$ and $R^b$ can be disposed meta to the cyclohexylidene bridging group. $R^a$ and $R^b$ can each independently be $C_{1-4}$ alkyl, $R^g$ can be $C_{1-4}$ alkyl, p and q can each be 0 or 1, and t is 0 to 5. $R^a$, $R^b$, and $R^g$ can be each methyl, r and s can be each 0 or 1, and t can be 0 or 3, specifically, 0.

Examples of other bisphenol carbonate units derived from bisphenol (4) wherein $X^b$ is a substituted or unsubstituted $C_{3-18}$ cycloalkylidene include adamantyl units (4f) and units (4g)

(4f)

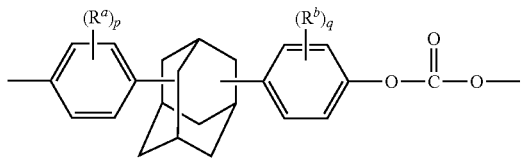

(4g)

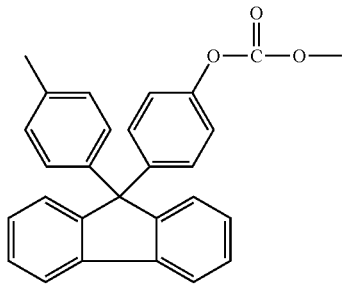

wherein $R^a$ and $R^b$ are each independently $C_{1-12}$ alkyl, and p and q are each independently 1 to 4. At least one of each of $R^a$ and $R^b$ can be disposed meta to the cycloalkylidene bridging group. $R^a$ and $R^b$ can each independently be $C_{1-3}$ alkyl, and p and q can be each 0 or 1. $R^a$, $R^b$ can be each methyl, p and q can each be 0 or 1. Carbonates containing units (4a) to (4g) are useful for making polycarbonates with high glass transition temperatures (Tg) and high heat distortion temperatures.

Other possible aromatic dihydroxy compounds of the formula HO—$R^1$—OH include compounds of formula (6)

(6)

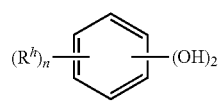

wherein each $R^h$ is independently a halogen atom, a $C_{1-10}$ hydrocarbyl such as a $C_{1-10}$ alkyl group, a halogen-substituted $C_{1-10}$ alkyl group, a $C_{6-10}$ aryl group, or a halogen-substituted $C_{6-10}$ aryl group, and n is 0 to 4. The halogen is usually bromine.

Some illustrative examples of specific aromatic dihydroxy compounds (herein also referred to as dihydroxy reactants) include the following: 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantane, alpha,alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like, or combinations comprising at least one of the foregoing dihydroxy compounds.

Specific examples of bisphenol compounds of formula (3) include 1,1-bis(4-hydroxyphenyl) methane, 1,1-bis(4-hydroxyphenyl) ethane, 2,2-bis(4-hydroxyphenyl) propane (hereinafter "bisphenol A" or "BPA"), 2,2-bis(4-hydroxyphenyl) butane, 2,2-bis(4-hydroxyphenyl) octane, 1,1-bis (4-hydroxyphenyl) propane, 1,1-bis(4-hydroxyphenyl) n-butane, 2,2-bis(4-hydroxy-2-methylphenyl) propane, 1,1-bis(4-hydroxy-t-butylphenyl) propane, 3,3-bis(4-hydroxyphenyl) phthalimidine, 2-phenyl-3,3-bis(4-hydroxyphenyl) phthalimidine (PPPBP), and 1,1-bis(4-hydroxy-3-methylphenyl)cyclohexane (DMBPC). Combinations comprising at least one of the foregoing dihydroxy compounds can also be used. The polycarbonate can be a linear homopolymer derived from bisphenol A, in which each of $A^1$ and $A^2$ can be p-phenylene, and $Y^1$ can be isopropylidene in formula (3).

"Polycarbonates" includes homopolycarbonates (wherein each $R^1$ in the polymer is the same), copolymers comprising different $R^1$ moieties in the carbonate ("copolycarbonates"), copolymers comprising carbonate units and other types of polymer units, such as ester units, and combinations comprising at least one of homopolycarbonates and/or copolycarbonates.

The polycarbonate can be made by a melt polymerization process, which can be a continuous melt process. Generally, in a melt polymerization process, polycarbonates can be prepared by co-reacting, in a molten state, a dihydroxy reactant and a diaryl carbonate (herein also referred to as a diaryl carbonate ester), such as diphenyl carbonate. The dihydroxy reactant and/or the diaryl carbonate ester can be added to the polymerization unit as a mixture with acetone. The dihydroxy reactant mixture and/or the diaryl carbonate ester mixture can have an acetone concentration of greater than 3 wt %, more specifically, greater than or equal to 5 wt %, and yet more specifically, more specifically, greater than or equal to 8 wt %, based upon a total weight of the mixture. Optionally, the upper limit of acetone in the mixture is based upon the desired transportation temperature, use of the acetone after transportation, and practicality such as sufficient dihydroxy or diaryl carbonate ester for use in subsequent reactions. Since the acetone can be used to make BPA, it can be beneficial to have the amount of acetone in the mixture near the stoichiometric amount for producing the BPA, wherein the stoichiometric amount is based upon weight. Excess acetone would entail unnecessary costs of transportation to the site and a need sell the surplus, while a deficiency would result in purchasing additional acetone to make up the difference, and will affect the needed transportation temperature of the mixture. Hence, the mixture can have a concentration of 3 to 35 wt % acetone, specifically, 5 to 30 wt % acetone, and more specifically, 10 to 25 wt % acetone or 20 to 35 wt % acetone, based upon a total weight of the mixture. The molar ratio of acetone to dihydroxy reactant can be greater than or equal to 0.1:1, specifically, 0.1:1 to 9:1. The molar ratio of dihydroxy reactant to diaryl carbonate ester to acetone can be stoichiometric in a mole ratio of 1:1:1. The acetone concentration can be adjusted before and/or during the reaction, e.g., by adding other component(s). Additional dihydroxy reactant and/or the diaryl carbonate ester can be added to attain and/or maintain the desired molar ratio between the dihydroxy reactant and the diaryl carbonate ester.

As acetone can be recovered from the polymerization unit (e.g., acetone can be recovered after the polycarbonate has been formed), the acetone does not need to be pre-separated prior to the addition of either or both of the dihydroxy reactant mixture and the diaryl carbonate ester mixture. In other words, the mixture is added to the polymerization unit and acetone is not separated from the mixture prior to the addition of the catalyst. As used herein, "not separated" refers to the acetone remaining in the vessel comprising the mixture. In other words, although the acetone may be present in a liquid or gaseous phase in the vessel, it is not withdrawn from the vessel, e.g., prior to the addition of the catalyst.

Acetone can be easily recovered due to the differences in volatilities between the dihydroxy reactant, the diaryl carbonate ester, the phenol byproduct, and the polymerized product at the operating conditions used in the polymerization unit (150° C.<T<320° C., 0.3 millibar absolute (mbara) <P<atmosphere (atm)). As such, acetone can optionally be recovered after the melt polymerization reaction forming the polycarbonate, e.g., from different sections of the polymerization unit. The separation device utilized to remove the acetone can be selected to avoid the loss of unreacted diaryl carbonate ester and any other volatile components from the reaction mixture. The separation device can optionally comprise single or multiple separation steps located after the polymerization unit.

A useful melt process for making polycarbonates could also use a diaryl carbonate ester having electron-withdrawing substituents on the aryls. Examples of specifically useful diaryl carbonate esters with electron withdrawing substituents include bis(4-nitrophenyl)carbonate, bis(2-chlorophenyl)carbonate, bis(4-chlorophenyl)carbonate, bis(methyl salicyl)carbonate, bis(4-methylcarboxylphenyl) carbonate, bis(2-acetylphenyl) carboxylate, bis(4-acetylphenyl) carboxylate, or a combination comprising at least one of the foregoing esters. The diaryl carbonate ester to dihydroxy reactant can be present in a molar ratio of 2:1 to 1:2, specifically, in a molar ratio of 1.5:1 to 1:1.5, more specifically, in a molar ratio of 1.05:1 to 1:1.05, even more specifically, in a molar ratio of 1:1.

In addition, transesterification catalyst(s) can be employed. Transesterification catalysts used in the melt transesterification polymerization production of polycarbonates can include alpha and/or beta catalysts. Beta catalysts are typically volatile and degrade at elevated temperatures. Beta catalysts are therefore preferred for use at early low-temperature polymerization stages. Alpha catalysts are typically more thermally stable and less volatile than beta catalysts.

The alpha catalyst can comprise a source of alkali or alkaline earth ions. The sources of these ions include alkaline earth hydroxides such as magnesium hydroxide and calcium hydroxide. Sources of alkali metal ions can include the alkali metal hydroxides such as illustrated by lithium hydroxide, sodium hydroxide, potassium hydroxide, and combinations comprising at least one of the foregoing. Examples of alkaline earth metal hydroxides are calcium hydroxide, magnesium hydroxide, and combinations comprising at least one of the foregoing. Of these, sodium hydroxide is particularly desirable. The alpha catalyst typically will be used in an amount sufficient to provide $1\times10^{-2}$ to $1\times10^{-8}$ moles, specifically, $1\times10^{-4}$ to $1\times10^{-7}$ moles of metal hydroxide per mole of the dihydroxy compounds employed. Other possible sources of alkaline earth and alkali metal ions include salts of carboxylic acids (such as sodium acetate) and derivatives of ethylene diamine tetraacetic acid (EDTA) (such as EDTA tetrasodium salt, and EDTA magnesium disodium salt), as well as combinations comprising at least one of the foregoing. For example, the alpha catalyst can comprise alkali metal salt(s) of a carboxylic acid, alkaline earth metal salt(s) of a carboxylic acid, or a combination comprising at least one of the foregoing. In another example, the alpha catalyst comprises Na$_2$Mg EDTA or a salt thereof.

The alpha transesterification catalyst can also, or alternatively, comprise salt(s) of a non-volatile inorganic acid. For example, the alpha catalyst can comprise salt(s) of a non-volatile inorganic acid such as NaH$_2$PO$_3$, NaH$_2$PO$_4$, Na$_2$HPO$_3$, KH$_2$PO$_4$, CsH$_2$PO$_4$, Cs$_2$HPO$_4$, and combinations comprising at least one of the foregoing. Alternatively, or in addition, the alpha transesterification catalyst can comprise mixed alkali metal salt(s) of phosphoric acid, such as NaKHPO$_4$, CsNaHPO$_4$, CsKHPO$_4$, and combinations comprising at least one of the foregoing.

Possible beta catalyst(s) can comprise a quaternary ammonium compound, a quaternary phosphonium compound, or a combination comprising at least one of the foregoing. The quaternary ammonium compound can be organic ammonium compound(s) having structure,

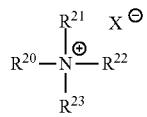

wherein R$^{20}$-R$^{23}$ independently a C$_1$-C$_{20}$ alkyl radical, C$_4$-C$_{20}$ cycloalkyl radical, or a C$_4$-C$_{20}$ aryl radical; and X$^-$ is an organic or inorganic anion. Optionally, anion X$^-$ can be selected from hydroxide, halide, carboxylate, sulfonate, sulfate, formate, carbonate, and bicarbonate. Some non-limiting examples of organic quaternary ammonium compounds include tetramethyl ammonium hydroxide, tetrabutyl ammonium hydroxide, tetramethyl ammonium acetate, tetramethyl ammonium formate, tetrabutyl ammonium acetate, and combinations comprising at least one of the foregoing. Tetramethyl ammonium hydroxide is often employed.

The quaternary phosphonium compound can be of organic phosphonium compounds having structure,

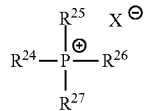

wherein R$^{24}$-R$^{27}$ are independently a C$^1$-C$^{20}$ alkyl radical, C$^4$-C$^{20}$ cycloalkyl radical, or a C$_4$-C$_{20}$ aryl radical; and X$^-$ is an anion (e.g., an organic or inorganic anion). Optionally, anion X$^-$ can be selected from hydroxide, halide, alkoxide, aryloxide, carboxylate, sulfonate, sulfate, formate, carbonate, and bicarbonate. Where X$^-$ is a polyvalent anion such as carbonate or sulfate it is understood that the positive and negative charges in the quaternary ammonium and phosphonium structures are properly balanced. For example, where R$^{20}$-R$^{23}$ are each methyl groups and X$^-$ is carbonate, it is understood that X$^-$ represents 2(CO$_3^{-2}$).

Examples of organic quaternary phosphonium compounds include tetramethyl phosphonium hydroxide, tetramethyl phosphonium acetate, tetramethyl phosphonium formate, tetrabutyl phosphonium hydroxide, tetrabutyl phosphonium acetate (TBPA), tetraphenyl phosphonium acetate, tetraphenyl phosphonium phenoxide, and combinations comprising at least one of the foregoing. TBPA is often employed.

The amount of beta catalyst employed is typically based upon the total number of moles of dihydroxy compound employed in the polymerization reaction. When referring to the ratio of beta catalyst, for example, phosphonium salt, to all dihydroxy compounds employed in the polymerization reaction, it is convenient to refer to moles of phosphonium salt per mole of the dihydroxy compound(s), meaning the number of moles of phosphonium salt divided by the sum of the moles of each individual dihydroxy compound present in the reaction mixture. The amount of beta catalyst (e.g., organic ammonium or phosphonium salts) employed typically will be 1×10$^{-2}$ to 1×10$^{-5}$, specifically, 1×10$^{-3}$ to 1×10$^{-4}$ moles per total mole of the dihydroxy compounds in the reaction mixture.

The method for producing a polycarbonate can comprise selecting a diaryl carbonate based on a maximum contaminant content and reacting the diaryl carbonate with a dihydroxy compound to form a melt polycarbonate comprising less than or equal to 500 ppb of molybdenum based on the total weight of the diaryl carbonate and the metal contaminant; and/or less than or equal to 33 ppb of vanadium based on the total weight of the diaryl carbonate and the metal contaminant; and/or less than or equal to 33 ppb of chromium based on the total weight of the diaryl carbonate and the metal contaminant; and/or less than or equal to 75 ppb of titanium based on the total weight of the diaryl carbonate and the metal contaminant; and/or less than or equal to 375 ppb of niobium based on the total weight of the diaryl carbonate and the metal contaminant; and/or less than or equal to 33 ppb of nickel based on the total weight of the diaryl carbonate and the metal contaminant; and/or less than or equal to 750 ppb of zirconium based on the total weight of the diaryl carbonate and the metal contaminant; and/or less or equal to 10 ppb iron based on the total weight of the diaryl carbonate and the metal contaminant.

The reacting can occur in a reactor, wherein the reactor comprises a reactor contaminant. The reactor contaminant can comprise molybdenum, vanadium, chromium, titanium, niobium, nickel, zirconium, iron, or a combination comprising one or more of the foregoing. The surface of the reactor in contact with the reaction, including any welds, can be free of nickel. The reactor can comprise a stainless steel reactor. The reactor can be passivated prior to the reacting, for example, with a strong acid such as nitric acid, citric acid, and the like.

The polymerization of the polycarbonate can comprise melt polymerizing the reactants in at least two polymerization units, in the presence of a catalyst composition, wherein the catalyst composition comprises an alpha catalyst; adding a quencher composition to the polycarbonate; mixing the quencher composition with the polycarbonate for a period of time of greater than or equal to 5 seconds prior to the addition to the polycarbonate of any additives having a reactive OH group or reactive ester group; filtering the polycarbonate; and directing the polycarbonate to an extruder.

The polycarbonate can be extruded in an extruder with a phosphorus-containing compound that has an abstractable proton and/or a hydrolyzable phosphate ester group, wherein the phosphorus-containing compound is compounded with the polycarbonate in an amount sufficient to result in an improvement in the color properties of the polycarbonate as compared to pellets formed from the same polycarbonate without addition of the phosphorus-containing compound. Examples of phosphorous-containing compounds are dimethyl phosphinic acid, dibutyl phosphinic acid, diphenyl phosphinic acid, 2-methylphenyl(phenyl)phosphinic acid, 3,5-dimethylphenyl(phenyl)phosphinic acid, 3-methoxyphenyl(phenyl)phosphinic acid, 4-methoxyphenyl(phenyl)phosphinic acid, 1-methylheptyl(phenyl)phosphinic acid, 4-ethoxyphenyl(phenyl)phosphinic acid, bis(4-methoxyphenyl)phosphinic acid, dioctylphosphinic acid, bis(2,4,4-trimethylpentyl)phosphinic acid, diammonium hydrogen phosphate, diphenyl phosphate, diphenyl phosphite, 4-(tert-pentyl)phenyl phosphate, (R)-(–)-1,1'-binaphthalene-2,2'-diyl hydrogen phosphate, and di(2-ethylhexyl)phosphate, mono-zinc phosphate $Zn(H_2PO_4)_2$, phosphoric acid, phosphorus acid, distearyl pentaerythritol diphosphite, n-butyl diphenylphosphinite, 2-phenylethyl diphenylphosphinate, 1-naphthyl diphenylphosphinate, methyl diphenylphosphinite, ethyl diphenylphosphinite, n-butyl diphenylphosphinite, methylcyclohexyl diphenylphosphinate, triphenyl phosphite, diisodecyl phenyl phosphite, tri-para-tolyl phosphate, tri-n-propyl phosphate, methyl diphenyl phosphate, tri-n-butyl phosphate, triphenyl phosphate, cyclohexyl diphenyl phosphate, bis(3,5-dimethylphenyl) 4-ethylphenyl phosphate, tris (3,4-dimethylphenyl)phosphate, tris(4-tert-butylphenyl) phosphate, trans-1,4-cyclohexanediol bis(diphenyl phosphate), trisnonylphenyl phosphate, triisodecyl phosphite, tris(tridecyl)phosphate, trilauryl phosphite, phosphorus pentoxide, pyrophosphoric acid, magnesium pyrophosphate, dimethyl acid pyrophosphate, diethyl acid pyrophosphate, potassium pyrophosphate, tetraethyl diphosphate, propylphosphonic anhydride, tris(N,N-tetramethylene)phosphoric acid triamide, methylphosphonic bis(dimethylamide), N,N,N',N'-tetramethylphosphorodiamidic chloride, hexamethylphosphoramide, 1,3-dimethyl-1,2,3,4-tetrahydro-1,3,2-benzodiazaphosphorine-2,4-dione, diphenyl 1-piperidinylphosphonate, phenyl N,N,N',N'-tetramethyldiamidophosphate, and N,N,N',N'-tetramethyl-P-phenylphosphonic diamide. The phosphorous-containing compound can comprise, for example, distearyl pentaerythritol diphosphite, phosphorous acid, or a combination comprising one or more of the foregoing.

The phosphorous-containing compound can be added in an amount of greater than or equal to 1 ppm, specifically, 5 to 9 ppm.

Polycarbonates polymerized from such a purified diaryl carbonate can have a yellowness index of, for example, less than or equal to 3, specifically, less than or equal to 2.5 as determined by ASTM D1925, after 2 hours of aging at 250° C.

The polycarbonate can have a light transparency of greater than 90% as determined using 3.2 mm thick samples using ASTM D1003-00, Procedure B using CIE standard illuminant C, with unidirectional viewing. Accordingly, when the polycarbonate has such a light transparency, it is herein referred to as an "optical grade" polycarbonate.

The polycarbonate can have an endcapping ratio (the ratio of the phenolic endgroups divided by the total endgroups times 100) of greater than or equal to 85%, specifically, greater than or equal to 90%, more specifically, greater than or equal to 95%. The polycarbonate can, in addition or alternatively, have a Fries less than 500 ppm by weight. The polycarbonate can, alternatively or in addition, have a weight average molecular weight of 13 to 18 kg/mol based on a polycarbonate standard.

The following examples are provided to illustrate the purification process. The examples are merely illustrative and are not intended to limit devices made in accordance with the disclosure to the materials, conditions, or process parameters set forth therein.

EXAMPLES

In the Examples 1-12, it is noted that metal contamination levels of the initial polycarbonate were not determined prior to spiking and that the metal levels as denoted in the figures are with regards to the amount of metal that was added to the initial polycarbonate. The yellowness indexes of the initial polycarbonate composition and of the spiked polycarbonate composition were measured in accordance with ASTM D1925. The determination of a significant increase in yellowness index was based on performing a hypothesis t-test with 95% confidence level, where a statistical difference between the yellowness indexes of the initial polycarbonate composition and of the spiked polycarbonate composition meant that there was a significant increase.

Example 1

Varying amounts of molybdenum (20 ppb, 50 ppb, 100 ppb, 250 ppb, 500 ppb, 750 ppb and 1000 ppb) were spiked into a polycarbonate resin that has an OQ grade (weight average molecular weight (MW) 32000-35000 grams per mole (g/mol) based on polystyrene (PS) standards) with solution yellowness index (YI) of 1.22 after 2 hours of aging at 250° C. Specifically, the molybdenum was incorporated into the resin by dissolving the OQ resin and known amounts of bis acetylacetonate dioxomolybdenum (VI) in dichloromethane. The dichloromethane was evaporated to obtain the intentionally contaminated resin. The yellowness index of the resulting polycarbonate after 2 hours of aging at 250° C. was determined versus the spiked molybdenum concentration, where the results are shown in FIG. 1.

FIG. 1 shows that polycarbonate compositions comprising greater than or equal to 50 ppb of spiked molybdenum resulted in compositions with a significantly higher YI than the original resin without any artificial contamination.

Example 2

Varying amounts of vanadium (20 ppb, 50 ppb, 100 ppb, 250 ppb, 500 ppb, 750 ppb and 1000 ppb) were added to a polycarbonate resin that has an OQ grade (MW 32000-35000 g/mol based on PS standards) with solution YI of 1.22 after 2 hours of aging at 250° C. Specifically, vanadium was incorporated into the resin by dissolving the OQ resin and known amounts of vanadium (III) acetyl acetonate in dichloromethane. The dichloromethane was evaporated to obtain the intentionally contaminated resin. The yellowness index of the resulting polycarbonate after 2 hours of aging at 250° C. was determined versus vanadium concentration, where the results are shown in FIG. 2.

Figure 2:
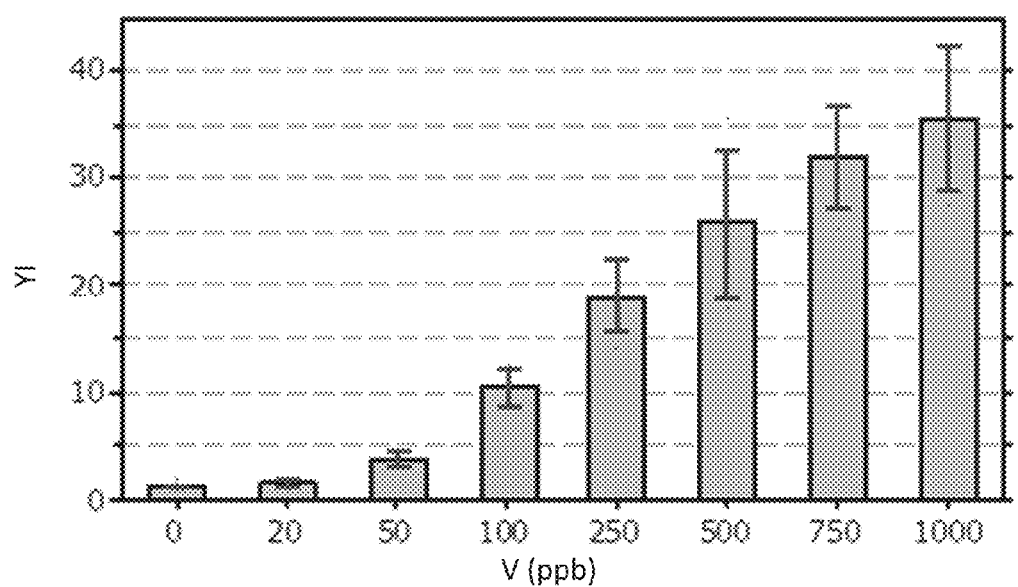
FIG. 2 is a graphical illustration of the effect of vanadium levels on yellowness index.

FIG. 2 shows that polycarbonate compositions comprising greater than or equal to 50 ppb of spiked vanadium resulted in compositions with a significantly higher YI than the original resin without any artificial contamination.

Example 3

Varying amounts of copper (20 ppb, 50 ppb, 100 ppb, 250 ppb, 500 ppb, 750 ppb and 1000 ppb) were added to a polycarbonate resin that has an OQ grade (MW 32000-35000 g/mol based on PS standards) with solution YI of 1.22 after 2 hours of aging at 250° C. Specifically, copper was incorporated into the resin by dissolving the OQ resin and known amounts of copper (II) acetyl acetonate in dichloromethane. The dichloromethane was evaporated to obtain the intentionally contaminated resin. The yellowness index of the resulting polycarbonate after 2 hours of aging at 250° C. was determined versus copper concentration, where the results are shown in FIG. 3.

Figure 3:
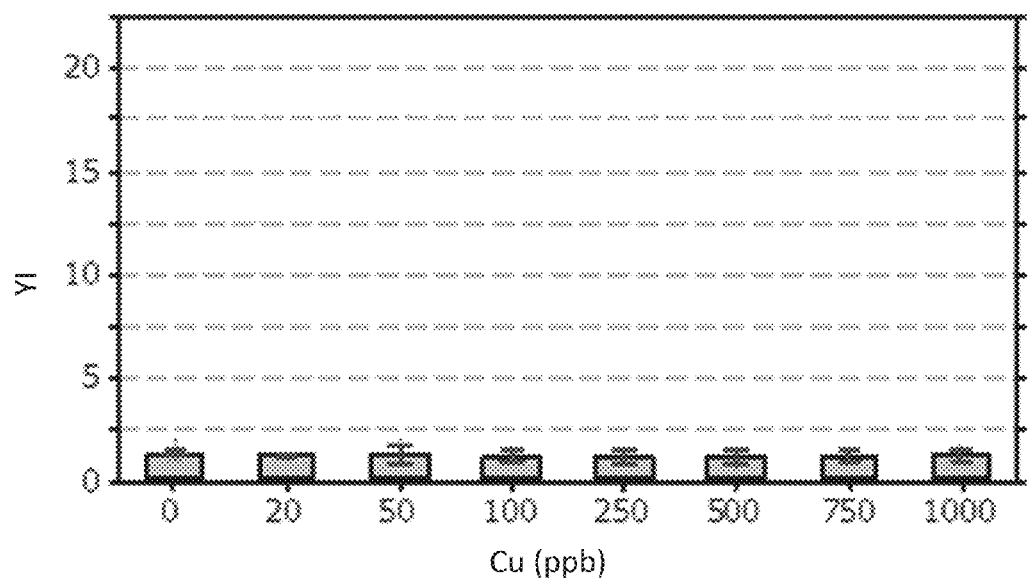
FIG. 3 is a graphical illustration of the effect of copper levels on yellowness index.

FIG. 3 shows that the yellowness index is virtually unaffected by copper in the polycarbonate compositions up to 1000 ppb.

Example 4

Varying amounts of chromium (20 ppb, 50 ppb, 100 ppb, 250 ppb, 500 ppb, 750 ppb and 1000 ppb) were added to a polycarbonate resin that has an OQ grade (MW 32000-35000 g/mol based on PS standards) with solution YI of 1.22 after 2 hours of aging at 250° C. Specifically, chromium was incorporated into the resin by dissolving the OQ resin and known amounts of chromium (III) acetyl acetonate in dichloromethane. The dichloromethane was evaporated to obtain the intentionally contaminated resin. The yellowness index of the resulting polycarbonate after 2 hours of aging at 250° C. was determined versus chromium concentration, where the results are shown in FIG. 4.

Figure 4:
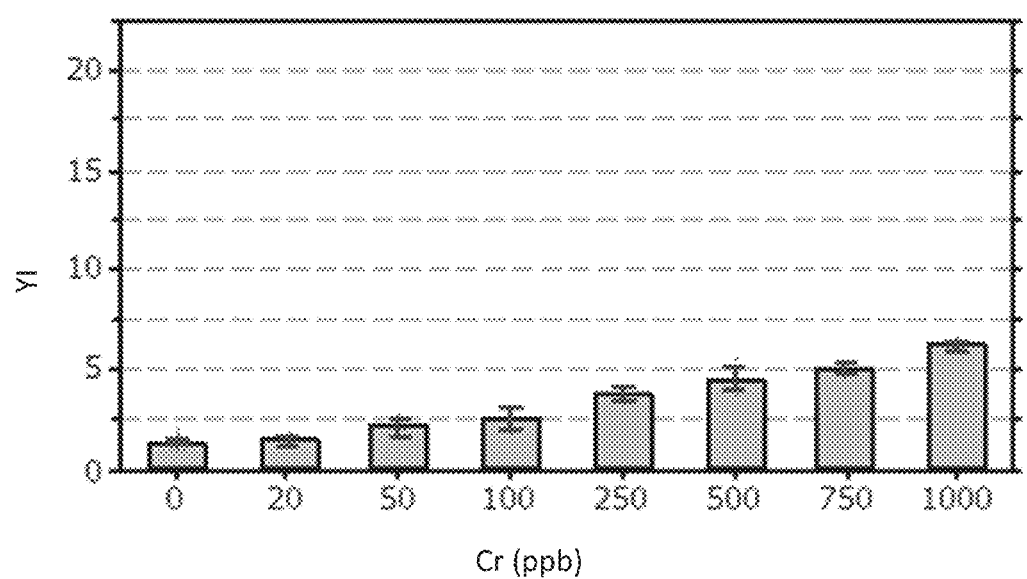
FIG. 4 is a graphical illustration of the effect of chromium levels on yellowness index.

FIG. 4 shows that polycarbonate compositions comprising greater than or equal to 50 ppb of spiked chromium resulted in compositions with a significantly higher YI than the original resin without any artificial contamination.

Example 5

Varying amounts of iron (20 ppb, 50 ppb, 100 ppb, 250 ppb, 500 ppb, 750 ppb and 1000 ppb) were added to a polycarbonate resin that has an OQ grade (MW 32000-35000 g/mol based on PS standards) with solution YI of 1.22 after 2 hours of aging at 250° C. Specifically, iron was incorporated into the resin by dissolving the OQ resin and known amounts of iron acetyl acetonate in dichloromethane. The dichloromethane was evaporated to obtain the intentionally contaminated resin. The yellowness index of the resulting polycarbonate after 2 hours of aging at 250° C. was determined versus copper concentration, where the results are shown in FIG. 5.

Figure 5:
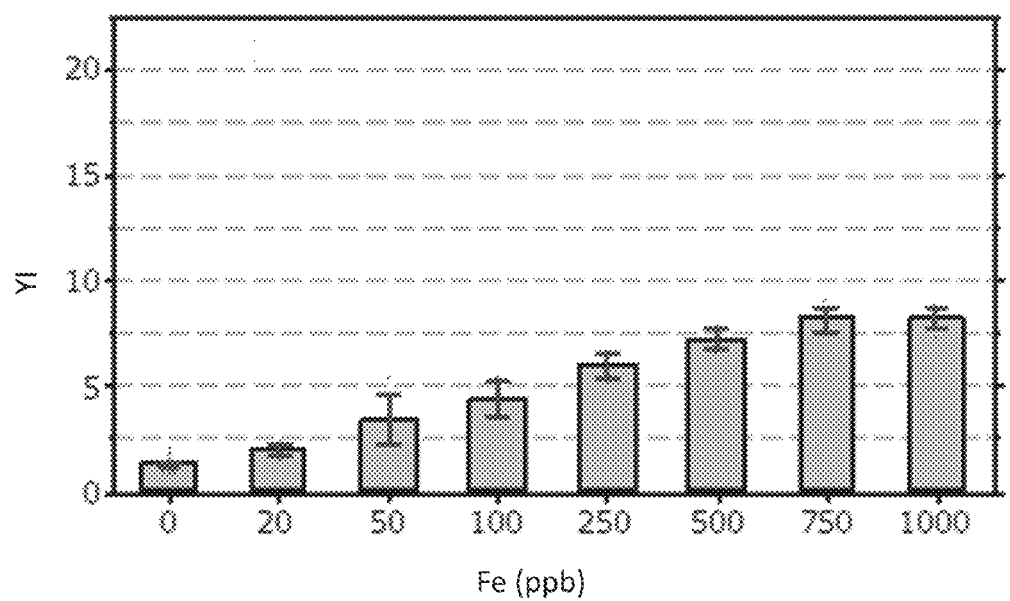
FIG. 5 is a graphical illustration of the effect of iron levels on yellowness index.

FIG. 5 shows that polycarbonate compositions comprising greater than or equal to 20 ppb of spiked iron resulted in compositions with a significantly higher YI than the original resin without any artificial contamination.

Example 6

Varying amounts of nickel (20 ppb, 50 ppb, 100 ppb, 250 ppb, 500 ppb, 750 ppb and 1000 ppb) were added to a polycarbonate resin that has an OQ grade (MW 32000-35000 g/mol based on PS standards) with solution YI of 1.22 after 2 hours of aging at 250° C. Specifically, nickel was incorporated into the resin by dissolving the OQ resin and known amounts of nickel (II) acetyl acetonate in dichloromethane. The dichloromethane was evaporated to obtain the intentionally contaminated resin. The yellowness index of the resulting polycarbonate after 2 hours of aging at 250° C. was determined versus copper concentration, where the results are shown in FIG. 6.

Figure 6:
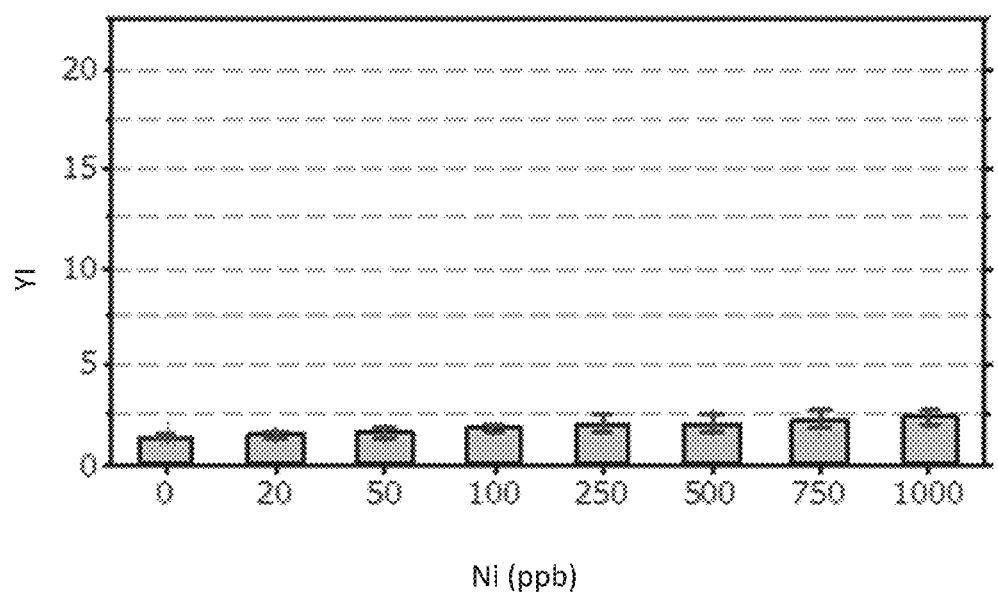
FIG. 6 is a graphical illustration of the effect of nickel levels on yellowness index.

FIG. 6 shows that polycarbonate compositions comprising greater than or equal to 50 ppb of spiked nickel resulted in compositions with a significantly higher YI than the original resin without any artificial contamination.

Example 7

Varying amounts of titanium (20 ppb, 50 ppb, 100 ppb, 250 ppb, 500 ppb, 750 ppb and 1000 ppb) were added to a polycarbonate resin that has an OQ grade (MW 32000-35000 g/mol based on PS standards) with solution YI of 1.22 after 2 hours of aging at 250° C. Specifically, titanium was incorporated into the resin by dissolving the OQ resin and known amounts of titanium isopropoxide in dichloromethane. The dichloromethane was evaporated to obtain the intentionally contaminated resin. The yellowness index of the resulting polycarbonate after 2 hours of aging at 250° C. was determined versus copper concentration, where the results are shown in FIG. 7.

Figure 7:
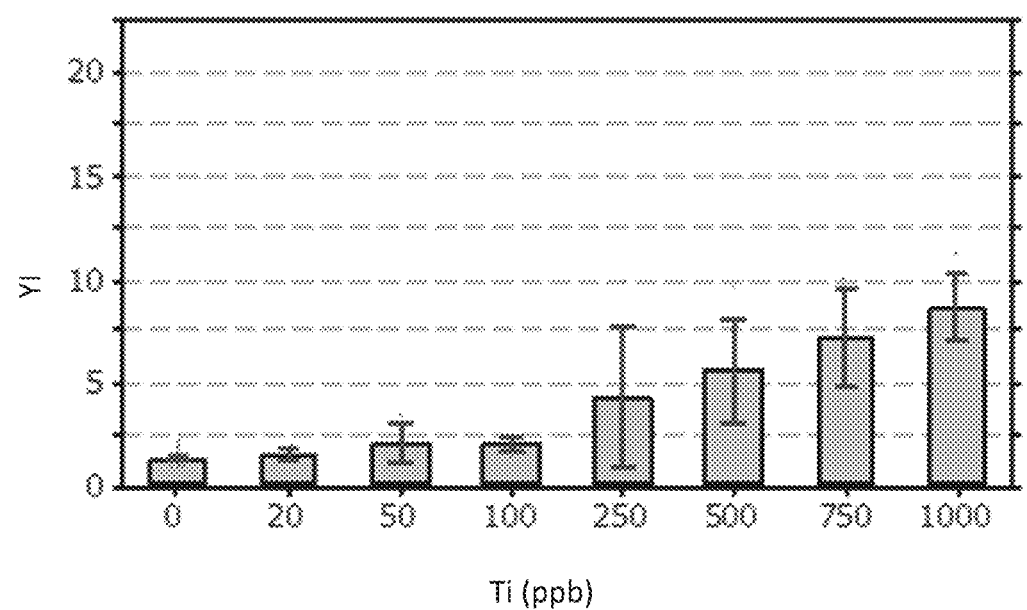
FIG. 7 is a graphical illustration of the effect of titanium levels on yellowness index.

FIG. 7 shows that polycarbonate compositions comprising greater than or equal to 100 ppb of spiked chromium resulted in compositions with a significantly higher YI than the original resin without any artificial contamination.

Example 8

Varying amounts of zirconium (20 ppb, 50 ppb, 100 ppb, 250 ppb, 500 ppb, 750 ppb and 1000 ppb) were added to a polycarbonate resin that has an OQ grade (MW 32000-35000 g/mol based on PS standards) with solution YI of 1.22 after 2 hours of aging at 250° C. Specifically, zirconium was incorporated into the resin by dissolving the OQ resin and known amounts of zirconium (IV) acetyl acetonate in dichloromethane. The dichloromethane was evaporated to obtain the intentionally contaminated resin. The yellowness index of the resulting polycarbonate after 2 hours of aging at 250° C. was determined versus zirconium concentration, where the results are shown in FIG. 8.

Figure 8:
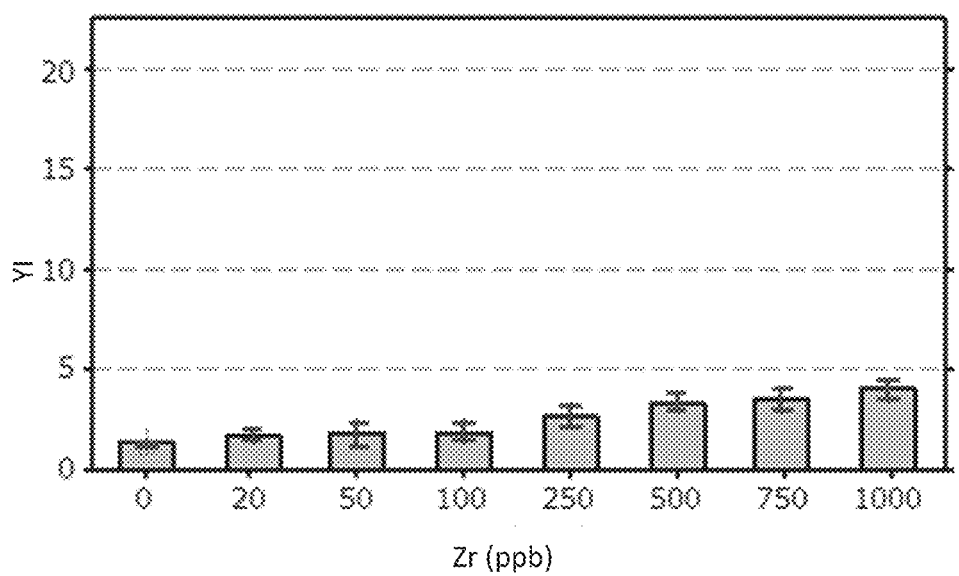
FIG. 8 is a graphical illustration of the effect of zirconium levels on yellowness index.

FIG. 8 shows that polycarbonate compositions comprising greater than or equal to 20 ppb of spiked zirconium resulted in compositions with a significantly higher YI than the original resin without any artificial contamination.

Example 9

Varying amounts of lead (20 ppb, 50 ppb, 100 ppb, 250 ppb, 500 ppb, 750 ppb and 1000 ppb) were added to a polycarbonate resin that has an OQ grade (MW 32000-35000 g/mol based on PS standards) with solution YI of 1.22 after 2 hours of aging at 250° C. Specifically, lead was incorporated into the resin by dissolving the OQ resin and known amounts of lead (II) acetyl acetonate in dichloromethane and a very small amount of acetic acid in order to improve solubility of lead (II) acetyl acetonate in the dichloromethane. The dichloromethane was evaporated to obtain the intentionally contaminated resin. The yellowness index of the resulting polycarbonate after 2 hours of aging at 250° C. was determined versus lead concentration, where the results are shown in FIG. 9.

Figure 9:
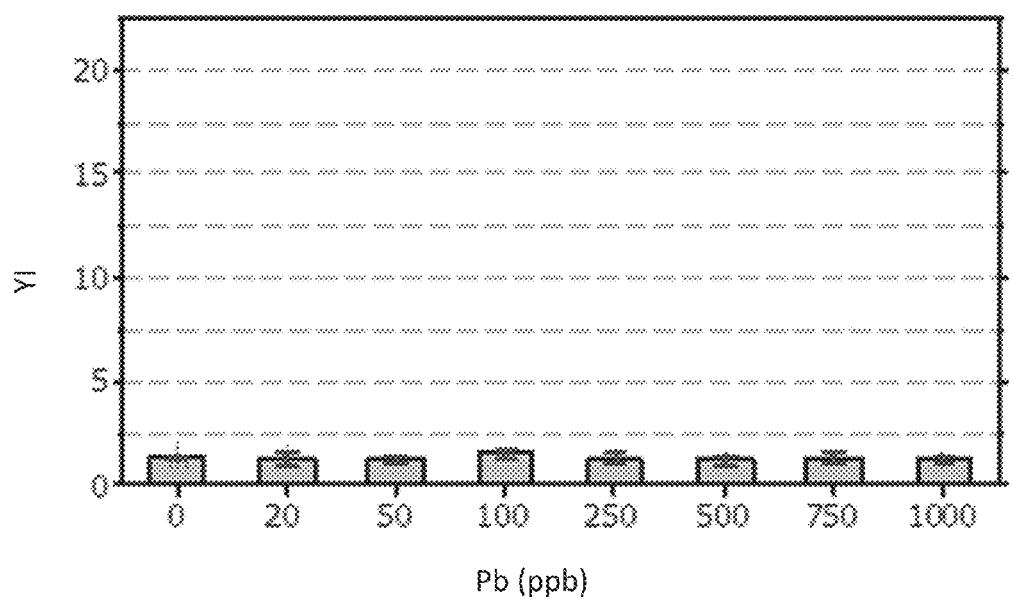
FIG. 9 is a graphical illustration of the effect of lead levels on yellowness index.

FIG. 9 shows that the yellowness index is virtually unaffected by lead in the polycarbonate compositions up to 1000 ppb.

Example 10

Varying amounts of bismuth (20 ppb, 50 ppb, 100 ppb, 250 ppb, 500 ppb, 750 ppb and 1000 ppb) were added to a polycarbonate resin that has an OQ grade (MW 32000-35000 g/mol based on PS standards) with solution YI of 1.22 after 2 hours of aging at 250° C. Specifically, bismuth was incorporated into the resin by dissolving the OQ resin and known amounts of bismuth (III) subsalicylate in dichloromethane and a very small amount of acetic acid in order to improve solubility of bismuth (III) subsalicylate in the dichloromethane. The dichloromethane was evaporated to obtain the intentionally contaminated resin. The yellowness index of the resulting polycarbonate after 2 hours of aging at 250° C. was determined versus bismuth concentration, where the results are shown in FIG. 10.

Figure 10:
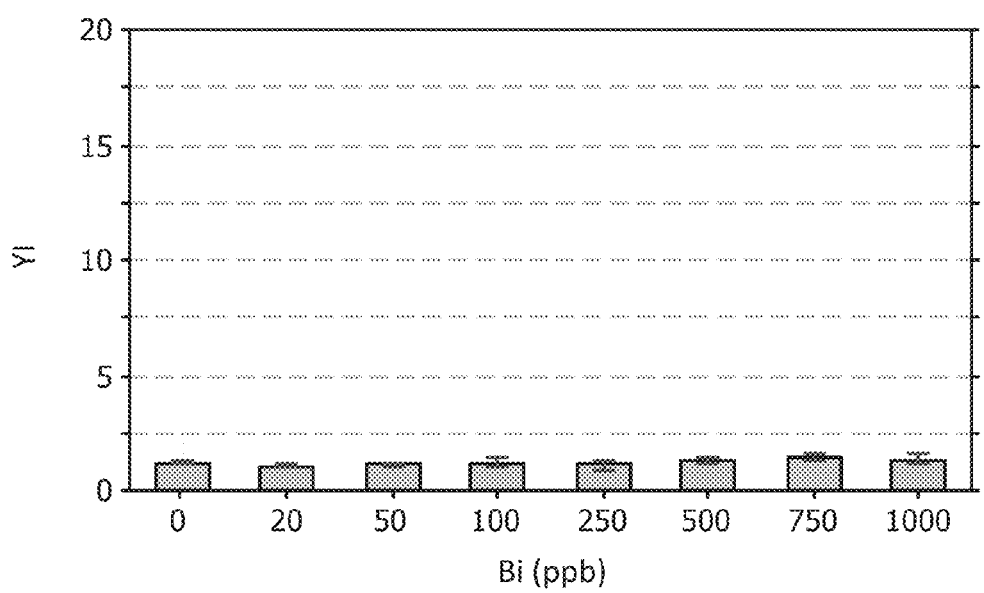
FIG. 10 is a graphical illustration of the effect of bismuth levels on yellowness index.

FIG. 10 shows that the yellowness index is virtually unaffected by bismuth in the polycarbonate compositions up to 1000 ppb.

Example 11

Varying amounts of tin (20 ppb, 50 ppb, 100 ppb, 250 ppb, 500 ppb, 750 ppb and 1000 ppb) were added to a polycarbonate resin that has an OQ grade (MW 32000-35000 g/mol based on PS standards) with solution YI of 1.22 after 2 hours of aging at 250° C. Specifically, tin was incorporated into the resin by dissolving the OQ resin and known amounts of tin (II) acetyl acetonate in dichloromethane and a very small amount of acetic acid in order to improve solubility of tin (II) acetyl acetonate in the dichloromethane. The dichloromethane was evaporated to obtain the intentionally contaminated resin. The yellowness index of the resulting polycarbonate after 2 hours of aging at 250° C. was determined versus tin concentration, where the results are shown in FIG. 11.

Figure 11:
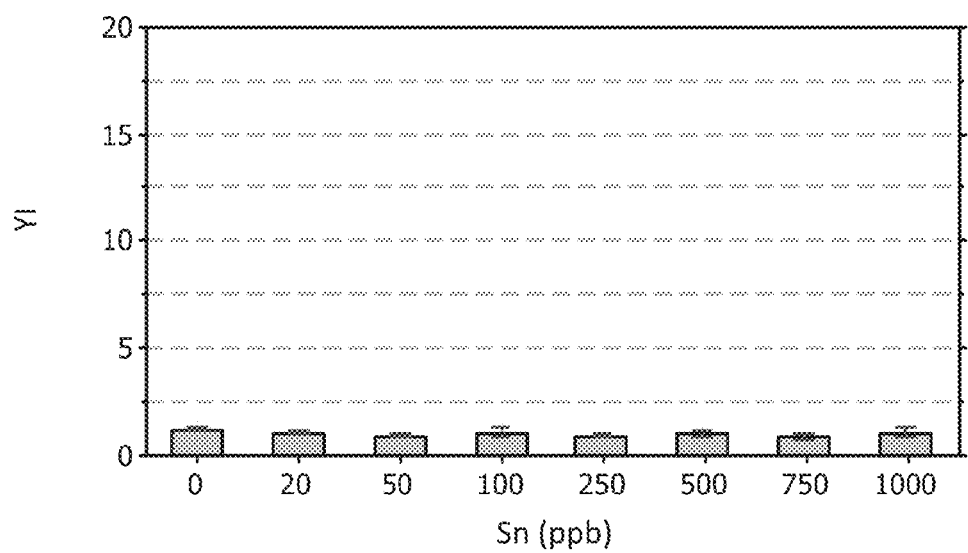
FIG. 11 is a graphical illustration of the effect of tin levels on yellowness index.

FIG. 11 shows that the yellowness index in virtually unaffected by tin in the polycarbonate compositions up to 1000 ppb.

Example 12

Varying amounts of niobium (20 ppb, 50 ppb, 100 ppb, 250 ppb, 500 ppb, 750 ppb and 1000 ppb) were added to a polycarbonate resin that has an OQ grade (MW 32000-35000 g/mol based on PS standards) with solution YI of 1.22 after 2 hours of aging at 250° C. Specifically, niobium was incorporated into the resin by dissolving the OQ resin and known amounts of niobium ethoxide in dichloromethane. The dichloromethane was evaporated to obtain the intentionally contaminated resin. The yellowness index of the resulting polycarbonate after 2 hours of aging at 250° C. was determined versus niobium concentration, where the results are shown in FIG. 12.

Figure 12:
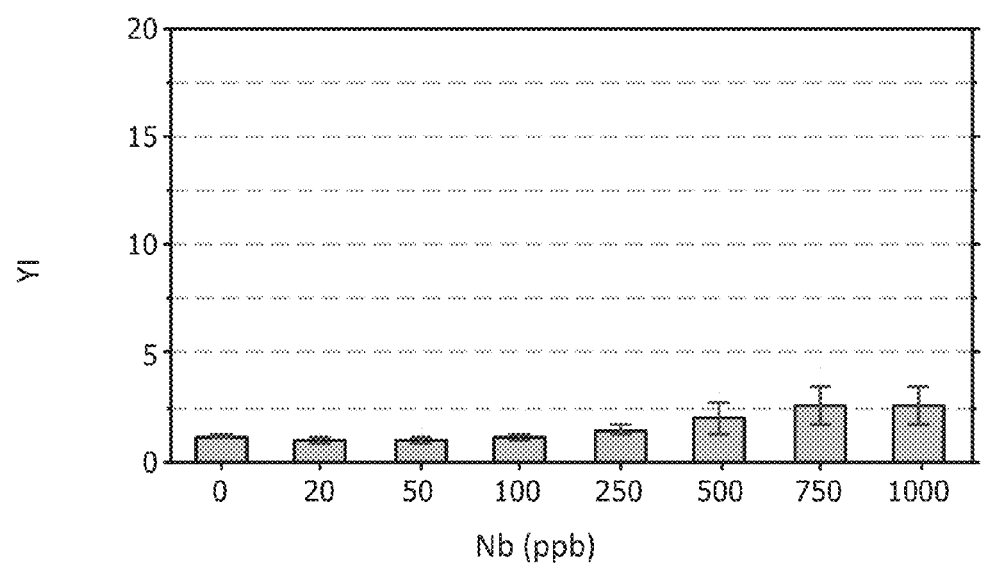
FIG. 12 is a graphical illustration of the effect of niobium levels on yellowness index.

FIG. 12 shows that polycarbonate compositions comprising greater than or equal to 500 ppb of spiked niobium resulted in compositions with a significantly higher YI than the original resin without any artificial contamination.

Example 13

Varying amounts of vanadium (20 ppb, 50 ppb, 100 ppb, and 200 ppb) were added to a melt polymerization of polycarbonate resin. Specifically, experiments were run in a continuous melt polycarbonate plant, where 58.7 kilograms per hour (kg/h) BPA, 55.1 kg/h of DPC, and a toluene solution comprising the respective amount of vanadium (III) acetyl acetonate to result in the specified amount of vanadium were fed into a continuously stirred formulation tank. The toluene solution was added to the formulation tank via an HPLC type dosing pump by Agilent (1100 Series). The formulation tank was operated at atmospheric pressure and 170° C. A 3.2 wt % aqueous solution of tetrabutyl phosphonium acetate was also added to the formulation tank at a rate of 123 milliliters per hour (mL/h).

The outlet stream of the formulation tank was then pumped to a continuously stirred reactor first reactor, which operated at 257° C. and 180 mbar vacuum in order to remove the reaction side-product, phenol. The vapor phase containing phenol and unreacted monomers BPA and DPC were continuously distilled in a scrubber where reflux ratio was adjusted so that the column head temperature was be 127° C. to yield high purity phenol. Unreacted BPA and DPC were fed back into the first reactor. In order to compensate for the DPC losses in the phenol overhead streams of the forthcoming reactors, an additional stream of DPC was added to the first reactor at 1.8 kg/h. An aqueous stream of 50 ppm $KNaH_2PO_4$ was also added in the first reactor at a flowrate of 1.9 milliliters per minute (mL/min).

The outlet stream of the first reactor was then pumped to a continuously stirred second reactor, which operated at 280° C. and 37 mbar vacuum. Due to the higher viscosity of this stream, a gear pump was used to convey the stream to the polymerization section where two horizontal polymerizers in series were used to reach the final polymer viscosity. The first polymerizer operated at 300° C. and 2.5-3.0 mbar vacuum. Phenol was removed and the continuous agitation was provided by a spectacle-type blade run at 20 revolutions per minute (rpm). The polymer stream was then pumped to the second polymerizer, which operated at 1.0-1.5 mbar and 302° C. The second polymerizer had a lattice-type agitator running at 8 rpm. The polymer was then fed from the second polymerizer to a 6 barrel twin screw finishing extruder (L/D=21, d=44 mm), where the barrel temperature was set at 300° C. and a spin rate of 100 rpm.

Figure 13:
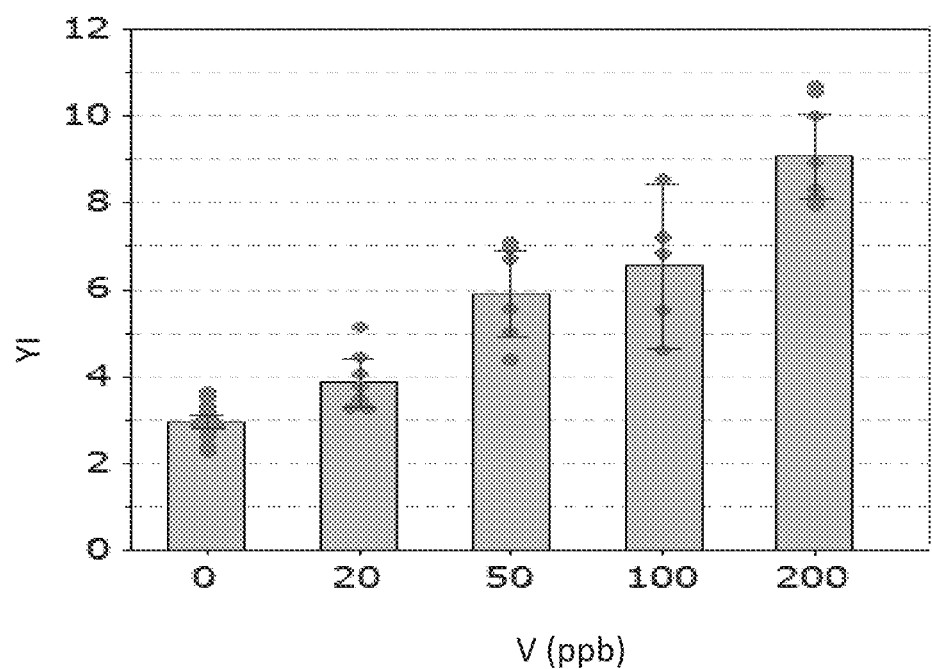
FIG. 13 is a graphical illustration of the effect of vanadium levels on yellowness index.

The yellowness index of the resulting polycarbonate after 2 hours of aging at 250° C. was determined versus vanadium concentration, where the results are shown in FIG. 13. FIG. 13 shows that polycarbonate compositions comprising greater than or equal to 20 ppb of spiked vanadium resulted in compositions with a significantly higher YI than the original resin without any contamination.

Set forth below are some embodiments of the method for making the polycarbonate disclosed herein and the polycarbonate made thereby.

Embodiment 1: a method for producing a polycarbonate comprising: reacting a diaryl carbonate with a dihydroxy compound to form a polycarbonate. The polycarbonate comprises: less than or equal to 500 ppb of molybdenum; less than or equal to 33 ppb of vanadium; less than or equal to 33 ppb of chromium; less than or equal to 75 ppb of titanium; less than or equal to 375 ppb of niobium; less than or equal to 33 ppb of nickel; less than or equal to 750 ppb of zirconium; and less or equal to 10 ppb iron.

Embodiment 2: a method for producing a polycarbonate comprising: reacting a diaryl carbonate with a dihydroxy compound to form a polycarbonate, wherein the diaryl carbonate comprises: less than or equal to 500 ppb of molybdenum; less than or equal to 38 ppb of vanadium; less than or equal to 38 ppb of chromium; less than or equal to 85 ppb of titanium; less than or equal to 425 ppb of niobium; less than or equal to 38 ppb of nickel; less than or equal to 12 ppb of zirconium; and less or equal to 12 ppb iron.

Embodiment 3: a method for producing a polycarbonate comprising: reacting a diaryl carbonate with a dihydroxy compound to form a polycarbonate. The polycarbonate comprises: less than or equal to 1,000 ppb of molybdenum; less than or equal to 33 ppb of vanadium; less than or equal to 33 ppb of chromium; less than or equal to 33 ppb of nickel; and less or equal to 10 ppb iron.

Embodiment 4: a method for producing a polycarbonate comprising: selecting a diaryl carbonate based on a maximum contaminant content and reacting the diaryl carbonate with a dihydroxy compound to form a melt polycarbonate comprising less than or equal to 500 ppb of molybdenum based on the total weight of the diaryl carbonate and the metal contaminant; less than or equal to 33 ppb of vanadium based on the total weight of the diaryl carbonate and the metal contaminant; less than or equal to 33 ppb of chromium based on the total weight of the diaryl carbonate and the metal contaminant; less than or equal to 75 ppb of titanium based on the total weight of the diaryl carbonate and the metal contaminant; less than or equal to 375 ppb of niobium based on the total weight of the diaryl carbonate and the metal contaminant; less than or equal to 33 ppb of nickel based on the total weight of the diaryl carbonate and the metal contaminant; less than or equal to 750 ppb of zirconium; and less or equal to 10 ppb iron based on the total weight of the diaryl carbonate and the metal contaminant. The reacting occurs in at least one reactor, wherein the reactor comprises a reactor contaminant.

Embodiment 5: the method of any of Embodiments 1-4, wherein the polycarbonate comprises less than or equal to 20 ppb chromium.

Embodiment 6: the method of any of Embodiments 1-5, wherein the polycarbonate comprises less than or equal to 20 ppb titanium.

Embodiment 7: the method of any of Embodiments 1-6, wherein the polycarbonate comprises less than or equal to 20 ppb nickel.

Embodiment 8: the method of any of Embodiments 1-7, wherein the polycarbonate comprises less than or equal to 5 ppb zirconium.

Embodiment 9: the method of any of Embodiments 1-8, wherein the polycarbonate comprises less than or equal to 20 ppb niobium.

Embodiment 10: the method of any of Embodiments 1-9, wherein the polycarbonate comprises less than or equal to 5 ppb iron.

Embodiment 11: the method of any of Embodiments 1-10, wherein the diaryl carbonate comprises diphenyl carbonate.

Embodiment 12: the method of any of Embodiments 1-11, wherein the dihydroxy compound is of the formula HO—$R^1$—OH, wherein $R^1$ is a $C_{6-30}$ aromatic group.

Embodiment 13: the method of any of Embodiments 1-12, wherein the polycarbonate has a yellowness index of less than or equal to 3 as determined by ASTM D1925, after 2 hours of aging at 250° C.

Embodiment 14: the method of any of Embodiments 1-13, wherein the polycarbonate has a yellowness index of less than or equal to 2.5 as determined by ASTM D1925, after 2 hours of aging at 250° C.

Embodiment 15: the method of any of Embodiments 1-14, further comprising preparing the diaryl carbonate.

Embodiment 16: the method of Embodiment 15, wherein the preparing comprises the step of decarbonylating a diaryl oxalate in the presence of a decarbonylation catalyst.

Embodiment 17: the method of Embodiment 16, wherein the diaryl oxalate has the formula: ArO(C=O)—(C=O) OAr, where each Ar independently is an aromatic hydrocarbon group having 6 to 14 carbon atoms.

Embodiment 18: the method of any of Embodiments 16-17, wherein the catalyst comprises an organic phosphorus compound.

Embodiment 19: the method of Embodiment 15, wherein the preparing comprises the reacting an aromatic hydroxy compound and carbon monoxide in the presence of oxygen and a catalyst.

Embodiment 20: the method of Embodiment 19 wherein the catalyst comprises a palladium catalyst.

Embodiment 21: the method of Embodiment 15, wherein the preparing comprises reacting an aromatic hydroxy compound with phosgene in the presence of a transesterification catalyst.

Embodiment 22: the method of Embodiment 15, wherein the preparing comprises reacting an aromatic hydroxy compound with a dialkyl carbonate in the presence of a transesterification catalyst.

Embodiment 23: the method of any of Embodiments 19-22, wherein the aromatic hydroxy compound has the formula (III)

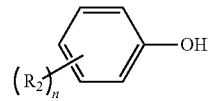

wherein n is an integer 1 to 3 and each $R_2$ is independently linear or branched, optionally substituted $C_{1-34}$ alkyl, specifically, $C_{1-6}$ alkyl, more specifically, $C_{1-4}$ alkyl; $C_{1-34}$ alkoxy, specifically, $C_{1-6}$ alkoxy, more specifically, $C_{1-4}$ alkoxy; $C_{5-34}$ cycloalkyl; $C_{7-34}$ alkylaryl; $C_{6-34}$ aryl; or a halogen radical, specifically, a chlorine radical. $R_2$ can also represent —COO—R', wherein R' can be H; optionally branched $C_{1-34}$ alkyl, specifically, $C_{1-6}$ alkyl, more specifically, $C_{1-4}$ alkyl; $C_{1-34}$ alkoxy, specifically, $C_{1-16}$ alkoxy, specifically, $C_{1-4}$ alkoxy; $C_{5-34}$ cycloalkyl; $C_{7-34}$ alkylaryl; or $C_{6-34}$ aryl.

Embodiment 24: the method of any of Embodiments 1-23, wherein the diaryl carbonate has the formula (I)

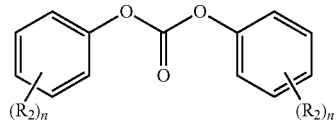

wherein n is an integer 1 to 3 and each $R_2$ is independently linear or branched, optionally substituted $C_{1-34}$ alkyl, specifically, $C_{1-6}$ alkyl, more specifically, $C_{1-4}$ alkyl; $C_{1-34}$ alkoxy, specifically, $C_{1-6}$ alkoxy, more specifically, $C_{1-4}$ alkoxy; $C_{5-34}$ cycloalkyl; $C_{7-34}$ alkylaryl; $C_{6-34}$ aryl; or a halogen radical, specifically, a chlorine radical. $R_2$ can also represent —COO—R', wherein R' can be H; optionally branched $C_{1-34}$ alkyl, specifically, $C_{1-6}$ alkyl, more specifically, $C_{1-4}$ alkyl; $C_{1-34}$ alkoxy, specifically, $C_{1-16}$ alkoxy, specifically, $C_{1-4}$ alkoxy; $C_{5-34}$ cycloalkyl; $C_{7-34}$ alkylaryl; or $C_{6-34}$ aryl.

Embodiment 25: the method of any of Embodiments 1-24, further comprising adding the diaryl carbonate and the dihydroxy compound to a polymerization unit before reacting, wherein the diaryl carbonate and/or the dihydroxy compound is added to the polymerization unit as a mixture with acetone.

Embodiment 26: the method of any of Embodiments 1-25, wherein the dihydroxy compound is bisphenol A, and further comprising forming the dihydroxy compound by: reacting phenol with acetone in the presence of a sulfur containing promoter to obtain a reaction mixture comprising bisphenol A, phenol, and the promoter; after reacting the phenol with the acetone, cooling the reaction mixture to form a crystal stream comprising crystals of bisphenol A and phenol; separating the crystals from the crystal steam; melting the crystals to form a molten stream of bisphenol A, phenol, and sulfur; contacting the molten stream with a base to reduce a sulfur concentration in the molten stream and form a reduced sulfur stream; and removing phenol from the reduced sulfur stream to form a bisphenol A product.

Embodiment 27: the method of Embodiment 26, wherein the molten stream is contacted with the base at a temperature of 70° C. to 120° C., or 80° C. to 100° C.

Embodiment 28: the method of any of Embodiments 26-27, wherein the promoter comprises a catalyst selected from 3-mercaptopropionic acid, methyl mercaptan, ethyl mercaptan, 2,2-bis(methylthio)propane, mercaptocarboxylic acid, and combinations comprising at least one of the foregoing promoters, for example, wherein the promoter comprises 3-mercaptopropionic.

Embodiment 29: the method of any of Embodiments 26-28, wherein the base comprises an alkali solution.

Embodiment 30: the method of any of Embodiments 26-29, wherein the base comprises an anion exchange resin, optionally the anion exchange resin comprises a tert-amine divinylbenzene/styrene ion exchange copolymer.

Embodiment 31: the method of any of Embodiments 26-30, wherein the sulfur concentration is reduced to 0.5 ppm to 15 ppm, or 2 ppm to 10 ppm, or 3 ppm to 8 ppm, based upon the weight of the bisphenol A.

Embodiment 32: the method of any of Embodiments 26-31, further comprising: prior to forming the crystal stream, cooling the reaction mixture to form an initial crystal stream comprising initial crystals of bisphenol A and phenol; separating the initial crystals from the initial crystal steam; melting the initial crystals to form an initial molten stream; and then performing the cooling to form the crystal steam in accord with Embodiment 25.

Embodiment 33: the method of any of Embodiments 1-32, wherein the polycarbonate comprises less than or equal to 20 ppb of molybdenum.

Embodiment 34: the method of any of Embodiments 4-33, wherein the reactor contaminant comprises molybdenum; vanadium; chromium; titanium; niobium; nickel; zirconium; iron; or a combination comprising one or more of the foregoing.

Embodiment 35: the method of any of Embodiments 4-34, wherein the surface of the reactor in contact with the reaction, including any welds, is free of nickel.

Embodiment 36: the method of any of Embodiments 4-35, wherein the reactor comprises a stainless steel reactor.

Embodiment 37: the method of Embodiment 36, further comprising passivating the stainless steel prior to the reacting with a strong acid such as nitric acid and/or citric acid.

Embodiment 38: the method of any of Embodiments 1-37, wherein the reacting comprises melt polymerizing the diaryl carbonate with the dihydroxy compound in at least two polymerization units, in the presence of a catalyst, wherein the catalyst composition comprises an alpha catalyst; adding a quencher composition to the polycarbonate; mixing the quencher composition with the polycarbonate for a period of time of greater than or equal to 5 seconds prior to the addition to the polycarbonate of any additives having a reactive OH group or reactive ester group; filtering the polycarbonate; and directing the polycarbonate to an extruder.

Embodiment 39: the method of any of Embodiments 1-38, wherein the polycarbonate comprises less than or equal to 38 ppb molybdenum and less than or equal to 10 ppb zirconium.

Embodiment 40: the method of any of Embodiments 1-39, wherein the polycarbonate comprises less than or equal to 33 ppb molybdenum and less than or equal to 10 ppb zirconium.

Embodiment 41: the method of any of Embodiments 1-40, wherein the polycarbonate comprises less than or equal to 20 ppb vanadium.

Embodiment 42: the polycarbonate made by the method of any of Embodiments 1-41.

Embodiment 43: a diaryl carbonate comprising: less than or equal to 500 ppb of molybdenum based on the total weight of the diaryl carbonate and the metal contaminant; less than or equal to 33 ppb of vanadium based on the total weight of the diaryl carbonate and the metal contaminant; less than or equal to 33 ppb of chromium based on the total weight of the diaryl carbonate and the metal contaminant; less than or equal to 75 ppb of titanium based on the total weight of the diaryl carbonate and the metal contaminant; less than or equal to 375 ppb of niobium based on the total weight of the diaryl carbonate and the metal contaminant; less than or equal to 33 ppb of nickel based on the total weight of the diaryl carbonate and the metal contaminant; less than or equal to 10 ppb of zirconium based on the total weight of the diaryl carbonate and the metal contaminant; and less or equal to 10 ppb iron based on the total weight of the diaryl carbonate and the metal contaminant.

Embodiment 44: the diaryl carbonate of Embodiment 43, wherein the diaryl carbonate comprises less than 20 ppb of vanadium based on the total weight of the diaryl carbonate and any metal contaminant.

Embodiment 45: a polycarbonate derived from the diaryl carbonate of any of Embodiments 43-44 and a dihydroxy compound.

Embodiment 46: the polycarbonate of any of Embodiments 42 and 45, wherein the polycarbonate has a light transparency of greater than 90% as determined using 3.2 mm thick samples using ASTM D1003-00, Procedure B using CIE standard illuminant C, with unidirectional viewing.

Embodiment 47: the polycarbonate of any of Embodiments 42 and 45-46, wherein the polycarbonate has one or more of an endcapping ratio (the ratio of the phenolic endgroups divided by the total endgroups times 100) of greater than or equal to 85%, a Fries less than 500 ppm by weight, a weight average molecular weight of 13 to 18 kg/mol based on a polycarbonate standard.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt %, or, more specifically, 5 wt % to 20 wt %", is inclusive of the endpoints and all intermediate values of the ranges of "5 wt % to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements can be combined in any suitable manner in the various embodiments. "Or" means "and/or" unless the context specifies otherwise.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A method for producing a polycarbonate comprising:
   reacting a diaryl carbonate with a dihydroxy compound to form a polycarbonate,
   wherein the polycarbonate comprising a metal contaminant comprises:
      less than or equal to 500 ppb of molybdenum based on the total weight of the diaryl carbonate and the metal contaminant;
      less than or equal to 33 ppb of vanadium based on the total weight of the diaryl carbonate and the metal contaminant;
      less than or equal to 33 ppb of chromium based on the total weight of the diaryl carbonate and the metal contaminant;
      less than or equal to 75 ppb of titanium based on the total weight of the diaryl carbonate and the metal contaminant;
      less than or equal to 375 ppb of niobium based on the total weight of the diaryl carbonate and the metal contaminant;
      less than or equal to 33 ppb of nickel based on the total weight of the diaryl carbonate and the metal contaminant;
      less than or equal to 750 ppb of zirconium based on the total weight of the diaryl carbonate and the metal contaminant; and
      less or equal to 10 ppb iron based on the total weight of the diaryl carbonate and the metal contaminant.

2. The method of claim 1, wherein the polycarbonate comprises less than or equal to 20 ppb vanadium and/or less than or equal to 20 ppb chromium and/or less than or equal to 20 ppb titanium and/or less than or equal to 20 ppb nickel and/or less than or equal to 10 ppb zirconium and/or less than or equal to 20 ppb niobium and/or less than or equal to 5 ppb iron.

3. The method of claim 1, wherein the diaryl carbonate comprises diphenyl carbonate.

4. The method of claim 1, wherein the dihydroxy compound is of the formula HO—$R^1$—OH, wherein $R^1$ is a $C_{6-30}$ aromatic group.

5. The method of claim 1, wherein the polycarbonate has a yellowness index of less than or equal to 3 as determined by ASTM D1925, after 2 hours of aging at 250° C.

6. The method of claim 1, further comprising preparing the diaryl carbonate.

7. The method of claim 6, wherein the preparing comprises the step of decarbonylating a diaryl oxalate in the presence of a decarbonylation catalyst.

8. The method of claim 7, wherein the diaryl oxalate has the formula: ArO(C=O)—(C=O)OAr, where each Ar independently is an aromatic hydrocarbon group having 6 to 14 carbon atoms.

9. The method of claim 6, wherein the preparing comprises the reacting an aromatic hydroxy compound and carbon monoxide in the presence of oxygen and a catalyst.

10. The method of claim 6, wherein the preparing comprises reacting an aromatic hydroxy compound with phosgene in the presence of a transesterification catalyst.

11. The method of claim 6, wherein the preparing comprises reacting an aromatic hydroxy compound with a dialkyl carbonate in the presence of a transesterification catalyst.

12. The method of claim 9, wherein the aromatic hydroxy compound has the formula (III)

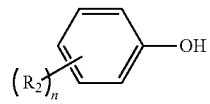

wherein n is an integer 1 to 3 and each $R_2$ is independently a $C_{1-34}$ alkyl, a $C_{1-34}$ alkoxy, a $C_{5-34}$ cycloalkyl, a $C_{7-34}$ alkylaryl, a $C_{6-34}$ aryl, a halogen radical, or —COO—R', wherein R' is H, a $C_{1-34}$ alkyl, $C_{1-34}$ alkoxy, $C_{5-34}$ cycloalkyl, $C_{7-34}$ alkylaryl, or $C_{6-34}$ aryl.

13. The method of claim 1, wherein the diaryl carbonate has the formula (I)

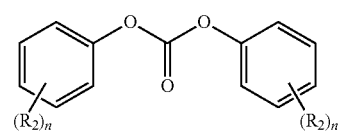

wherein n is an integer 1 to 3 and each $R_2$ is independently, a $C_{1-34}$ alkyl, a $C_{1-34}$ alkoxy, a $C_{5-34}$ cycloalkyl, a $C_{7-34}$ alkylaryl; a $C_{6-34}$ aryl; a halogen radical, or —COO—R', wherein R' is H, a $C_{1-34}$ alkyl, a $C_{1-34}$ alkoxy, a $C_{5-34}$ cycloalkyl, a $C_{7-34}$ alkylaryl; or a $C_{6-34}$ aryl.

14. The method of claim 1, further comprising adding the diaryl carbonate and the dihydroxy compound to a polymerization unit before reacting, wherein the diaryl carbonate and/or the dihydroxy compound is added to the polymerization unit as a mixture with acetone.

15. The method of claim 1, wherein the dihydroxy compound is bisphenol A, and further comprising forming the dihydroxy compound by:
   reacting phenol with acetone in the presence of a sulfur containing promoter to obtain a reaction mixture comprising bisphenol A, phenol, and the promoter;
   after reacting the phenol with the acetone, cooling the reaction mixture to form a crystal stream comprising crystals of bisphenol A and phenol;
   separating the crystals from the crystal steam; melting the crystals to form a molten stream of bisphenol A, phenol, and sulfur;
   contacting the molten stream with a base to reduce a sulfur concentration in the molten stream and form a reduced sulfur stream; and
   removing phenol from the reduced sulfur stream to form a bisphenol A product.

16. The method of claim 15, further comprising:
   prior to forming the crystal stream, cooling the reaction mixture to form an initial crystal stream comprising initial crystals of bisphenol A and phenol;
   separating the initial crystals from the initial crystal steam;
   melting the initial crystals to form an initial molten stream; and
   then performing the cooling to form the crystal steam in accord with Embodiment 25.

17. The method of claim 1, further comprising extruding the polycarbonate, wherein phosphorous acid is added to the extruder.

18. The polycarbonate made by the method of claim 1.

19. A diaryl carbonate comprising a metal contaminant comprising:

less than or equal to 500 ppb of molybdenum based on the total weight of the diaryl carbonate and the metal contaminant;

less than or equal to 33 ppb of vanadium based on the total weight of the diaryl carbonate and the metal contaminant;

less than or equal to 33 ppb of chromium based on the total weight of the diaryl carbonate and the metal contaminant;

less than or equal to 75 ppb of titanium based on the total weight of the diaryl carbonate and the metal contaminant;

less than or equal to 375 ppb of niobium based on the total weight of the diaryl carbonate and the metal contaminant;

less than or equal to 33 ppb of nickel based on the total weight of the diaryl carbonate and the metal contaminant;

less than or equal to 10 ppb of zirconium based on the total weight of the diaryl carbonate and the metal contaminant; and less or equal to 10 ppb iron based on the total weight of the diaryl carbonate and the metal contaminant.

20. The diaryl carbonate of claim 19, wherein the diaryl carbonate comprises less than 20 ppb of vanadium based on the total weight of the diaryl carbonate and any metal contaminant.

21. A method for producing a polycarbonate comprising: reacting a diaryl carbonate with a dihydroxy compound to form a polycarbonate, wherein the polycarbonate comprises: less than or equal to 1,000 ppb of molybdenum; less than or equal to 33 ppb of vanadium; less than or equal to 33 ppb of chromium; less than or equal to 33 ppb of nickel; and less or equal to 10 ppb iron.

22. A method for producing a polycarbonate comprising: selecting a diaryl carbonate based on a maximum contaminant content and reacting the diaryl carbonate with a dihydroxy compound to form a melt polycarbonate comprising a metal contaminant comprising less than or equal to 500 ppb of molybdenum based on the total weight of the diaryl carbonate and the metal contaminant; less than or equal to 33 ppb of vanadium based on the total weight of the diaryl carbonate and the metal contaminant; less than or equal to 33 ppb of chromium based on the total weight of the diaryl carbonate and the metal contaminant; less than or equal to 75 ppb of titanium based on the total weight of the diaryl carbonate and the metal contaminant; less than or equal to 375 ppb of niobium based on the total weight of the diaryl carbonate and the metal contaminant; less than or equal to 33 ppb of nickel based on the total weight of the diaryl carbonate and the metal contaminant; less than or equal to 10 ppb of zirconium based on the total weight of the diaryl carbonate and the metal contaminant; and less or equal to 10 ppb iron based on the total weight of the diaryl carbonate and the metal contaminant; wherein the reacting occurs in at least one reactor, and wherein the reactor comprises a reactor contaminant.

* * * * *